(12) United States Patent
Chandra S R et al.

(10) Patent No.: US 11,837,341 B1
(45) Date of Patent: Dec. 5, 2023

(54) SECURED MESSAGING SERVICE WITH CUSTOMIZED NEAR REAL-TIME DATA INTEGRATION

(71) Applicant: CERNER INNOVATION, INC., Kansas City, KS (US)

(72) Inventors: Nithin Chandra S R, Bangalore (IN); Archana Tavaragiri, Bangalore (IN)

(73) Assignee: Cerner Innovation, Inc., Kansas City, MO (US)

( * ) Notice: Subject to any disclaimer, the term of this patent is extended or adjusted under 35 U.S.C. 154(b) by 1058 days.

(21) Appl. No.: 15/651,130

(22) Filed: Jul. 17, 2017

(51) Int. Cl.
| G16H 10/60 | (2018.01) |
| H04L 9/40 | (2022.01) |
| G06F 3/048 | (2013.01) |
| G06F 21/31 | (2013.01) |
| G06F 40/205 | (2020.01) |
| G10L 15/26 | (2006.01) |

(52) U.S. Cl.
CPC ............ *G16H 10/60* (2018.01); *G06F 3/048* (2013.01); *G06F 21/31* (2013.01); *G06F 40/205* (2020.01); *G10L 15/26* (2013.01); *H04L 63/0428* (2013.01); *H04L 63/08* (2013.01)

(58) Field of Classification Search
CPC ........ G06Q 50/22; G06Q 50/24; G06F 19/00; G06F 19/32; G06F 19/34; G06F 19/3418; G06F 19/36; G06F 21/31; G06F 3/048; G06F 17/2705; G16H 10/00; G16H 10/60; G16H 15/00; G16H 30/00; G16H 50/00; G16H 50/20; G16H 50/50; G16H 80/00; H04L 63/08; H04L 63/0428; G10L 15/265

USPC ......................................................... 705/2, 3
See application file for complete search history.

(56) References Cited

U.S. PATENT DOCUMENTS

| 6,383,135 | B1 * | 5/2002 | Chikovani | G16H 20/00 128/920 |
| 7,499,048 | B2 * | 3/2009 | Sieracki | A61B 5/00 700/17 |
| 8,117,048 | B1 * | 2/2012 | Rzadkiewicz | G16H 40/67 600/300 |
| 8,311,848 | B2 * | 11/2012 | Subash | G06Q 10/10 705/2 |
| 8,712,791 | B2 * | 4/2014 | Dahlin | G16H 10/60 705/2 |
| 10,483,003 | B1 * | 11/2019 | McNair | G16H 10/60 |
| 2004/0189718 | A1 * | 9/2004 | Stein | G06Q 10/10 715/853 |
| 2005/0015115 | A1 * | 1/2005 | Sullivan | A61B 5/7475 607/5 |

(Continued)

*Primary Examiner* — Jason S Tiedeman
(74) *Attorney, Agent, or Firm* — Invoke

(57) ABSTRACT

The present invention is directed to a secure messaging assistant that provides secure two-way communications between a user device and a server. The user can conduct a natural language conversation with the secure messaging assistant ask medical questions and enter symptoms that the user is experiencing. The secure messaging assistant uses natural language processing to return, in near real-time, medical conditions that are responsive to the user's input and which account for the user's own medical history (e.g., securely stored electronic medical history). The secure messaging assistant prevents the user from disclosing private or sensitive information to an internet based search engine, in the quest for medical advice.

23 Claims, 20 Drawing Sheets

(56) References Cited

U.S. PATENT DOCUMENTS

| | | | |
|---|---|---|---|
| 2005/0039127 A1* | 2/2005 | Davis | G16H 40/20 715/708 |
| 2008/0251579 A1* | 10/2008 | Larsen | G16H 40/20 235/380 |
| 2008/0273774 A1* | 11/2008 | Mikhail | G16H 30/40 382/128 |
| 2014/0006055 A1* | 1/2014 | Seraly | G06Q 10/10 705/3 |
| 2014/0019128 A1* | 1/2014 | Riskin | G16H 10/60 704/235 |
| 2014/0297318 A1* | 10/2014 | Prasad | G06Q 10/1095 705/3 |
| 2014/0351232 A1* | 11/2014 | Fan | G06Q 10/06314 707/706 |
| 2014/0365242 A1* | 12/2014 | Neff | G06Q 50/22 705/3 |
| 2015/0081338 A1* | 3/2015 | Lai | G16H 40/67 705/2 |
| 2015/0112709 A1* | 4/2015 | Bowman | H04L 67/18 705/2 |
| 2015/0149203 A1* | 5/2015 | Csurka | G16H 10/60 705/3 |
| 2015/0248536 A1* | 9/2015 | Tawil | G16H 30/20 705/3 |
| 2015/0278483 A1* | 10/2015 | Pruitt | G16H 10/60 705/3 |
| 2015/0370979 A1* | 12/2015 | Boloor | G16H 40/20 705/3 |
| 2016/0004831 A1* | 1/2016 | Carlson | G16H 10/20 705/2 |
| 2016/0078181 A1* | 3/2016 | Tanner, Jr. | G16H 40/20 705/2 |
| 2016/0283667 A1* | 9/2016 | Rachapalli | G16H 10/60 |
| 2016/0350564 A1* | 12/2016 | Nedelcu | G16H 40/67 |
| 2016/0371446 A1* | 12/2016 | Otin | G16H 50/20 |
| 2017/0143249 A1* | 5/2017 | Davis | G10L 19/018 |
| 2017/0169168 A1* | 6/2017 | Batchelor | G06Q 10/10 |
| 2017/0177813 A1* | 6/2017 | Yao | G16H 50/20 |
| 2017/0337651 A1* | 11/2017 | Lese | G16H 40/67 |
| 2018/0067986 A1* | 3/2018 | Gupta | G06F 3/04842 |

* cited by examiner

```
@{
    ViewBag.Title = "Get Patient Details";
    Layout = "~/Views/Shared/_Layout.cshtml";
}

@section head
    {

<link rel="icon" href="~/favicon.ico" type="image/x-icon">
    <link href="~/Content/boostrap.min.css" rel="stylesheet" />
    <link href="~/Content/master.css" rel="stylesheet" />
    <link href="https://maxcdn.bootstrapcdn.com/font-awesome/4.3.0/css/font-awesome.min.css" rel="stylesheet">

}

@section javascript
{
    <script src="http://code.jquery.com/jquery-1.10.2.min.js"></script>
    <script src="http://netdna.bootstrapcdn.com/bootstrap/3.3.4/js/bootstrap.min.js"></script>
    <script src="~/Scripts/Patient.js"></script>

}
<body>
    <div class="container">
        <div class="panel panel-height">
            <img src="~/images/logo.png" alt="logo" class="logo">
            <div class="center-block">
                <div class="input-group pad-hor">
                    <input type="text" class="form-control" id="txtPtntId" placeholder="Get Patient Details by ID">
                    <span class="input-group-btn">
                        <button type="button" class="btn btn-default" onclick="getPatientDetails();">Go!</button>
                    </span>
                </div><!-- /input-group -->
            </div>
        </div>
    </div>
</body>
```

*FIG. 4.*

```
@{
    ViewBag.Title = "Patient Information";
    Layout = "~/Views/Shared/_Layout.cshtml";
}

@section head
{
    <link rel="icon" href="~/favicon.ico" type="image/x-icon">
    <link href="~/Content/bootstrap.min.css" rel="stylesheet" />
    <link href="~/Content/master.css" rel="stylesheet" />
    <link href="https://maxcdn.bootstrapcdn.com/font-awesome/4.3.0/css/font-awesome.min.css" rel="stylesheet">
}

@section javascript
{
    <script src="http://code.jquery.com/jquery-1.10.2.min.js"></script>
    <script src="http://netdna.bootstrapcdn.com/bootstrap/3.3.4/js/bootstrap.min.js"></script>
    <script src="~/Scripts/Patient.js"></script>
    <script src="~/Scripts/Chat.js"></script>

}

<div class="container">
    <div>
        <div class="panel">
            <!--Heading-->
            <div class="panel-heading demographics">
                <div class= "pull-left">
                    <p>Name: <strong>@ViewBag.PatientName</strong></p>
                    <p>Gender: <strong>@ViewBag.Gender</strong> DOB: <strong>@ViewBag.DOB</strong>  Age:<strong>@ViewBag.Age</strong> yrs </div>
                <div class="nav">
                    <a href="#" onclick="javascript:redirectToHome();" class="pull-right"> <span class="glyphicon glyphicon-home" aria-hidden="true"></span></a>
                    <a href="" data-toggle="modal" data-target="#myModal" class="pull-right"> <span class="glyphicon glyphicon-info-sign" aria-hidden="true"></span></a>
                </div>
            </div>
            <!-- Modal -->
            <div class="modal fade" id="myModal" tabindex="-1" role="dialog" aria-labelledby="myModalLabel">
                <div class="modal-dialog" role="document">
                    <div class="modal-content">
                        <div class="modal-header">
                            <button type="button" class="close" data-dismiss="modal" aria-label="Close"><span aria-hidden="true">×</span></button>
                            <h4 class="modal-title" id="myModalLabel">About Health Chat</h4>
                        </div>
                        <div class="modal-body">
```

*FIG. 6.*

```
using System;
using System.Collections.Generic;
using System.Linq;
using System.Web;
using System.Web.Mvc;
using System.Web.Http;
using System.Configuration;
using Hl7.Fhir;
using Hl7.Fhir.Model;
using Hl7.Fhir.Rest;
using Hl7.Fhir.Serialization;

Namespace MvcApplication4.Controllers
{
    public class HomeController : Controller
    {
        public static string pid = "";
        public string fhirUrl = "https://fhir-open-api-dstu2.smarthealthit.org";
        public string patientName = "";
        public ActionResult splash()
        {
            return View();
        }

/// <param name= "patientId"></param>
        /// <returns></returns>
        public ActionResult patient([System.Web.Http.FromUri]string patientId)
        {
            string data = String.Concat("Patient/". patientId);
            pid = data;
            getPatientInfo();
            return View();
        } public ActionResult Chat()
        { getPatientInfo();
            return View();
        } public void getPatientInfo()
        {
            var patientData = new FhirClient(fhirUrl);
            var patData = patientData.Read<Patient>(pid);
            try
            { foreach (var i in patData.Name)
                {
```

FIG. 7.

```
using System;
using System.Collections.Generic;
using System.Linq;
using System.Web;

Namespace MvcApplication4.Models
{
      public class Patient
      { public Dictionary<string, List<string>> sympDiag = new Dictionary<string, List<string>>();

public Patient()
            {

//sympDiag.Add("Headache", new List<string>() { "Acute sinusitis", "Migraine with aura" });
                  //   sympDiag.Add("Headache", new List<string>());
                  //   sympDiag.Add("Upper Back Pain", new List<string> { "Abdominal Pain" });
                  //   sympDiag.Add("Fever", new List<string> { "Diarrhea", "Pneumonia" });
                  //   sympDiag.Add("Chest Pain", new List<string> { "Pure hypercholesterolmia" });
            }
      }

```
var pathName = "/" + window.location.pathname.split('/')[1];
var connString = window.location.protocol.replace(/\:g, '') + "://" +
window.location.host + pathName;

function showChatPage() {
    top.location.href = connString + "/Home/Chat";

} function setActiveClass(spanId) { if ($('#' + spanID.id).hasClass("label-default")) {
        $('#' + spanID.id).removeClass("label-default");
        $('#' + spanID.id).addClass("label-success");
    } else {
        $('#' + spanID.id).removeClass("label-success");
        $('#' + spanID.id).addClass("label-default");
    }
} function getConditions() { var selClass = document.getElementsByClassName("label-success");
    var sympValue = new Array();
    for (var i = 0; i < selClass.length; i++) {
        sympValue.push(selClass[i].innerHTML);
    } var temp = '<ul>';
    for (var i + 0; i < sympValue.length; i++) {
        temp += '<li>' + sympValue[i] + '</li>'
    }
    temp += '</ul>';

$('#sympList').show();
    $('#sympDiv').append(temp);

var url = connString + '/api/Service/GetConditions/GetConditions?symptoms=' +
sympValue;

$.ajax({
        type: "GET",
        cache: false,
        async: true,
        contentType: 'application/json;charset="utf-8"',
        dataType: 'json',
        url: url,
        success: function (data) {
            setTimeout(function () { getData(data); }, 2000);
        },
```

function getData(data) {

$('#waitforData').show();
    setTimeout(function () { diagList(data); }, 3000);

} function diagList(data) { var temp = '<ul>';
    for (var i = 0; i < data.length; i++) {
        temp += '<li>' + data[i] + '</li>'
    } temp += '</ul>';
    $('#diagList').show();
    $('#dispDiag').append(temp);
    $('#lstOk').show();
    setTimeout(bookAppt, 2000);
} function bookAppt() {
    $('#bookAppt').show();
}

SECURED MESSAGING SERVICE WITH CUSTOMIZED NEAR REAL-TIME DATA INTEGRATION

CROSS-REFERENCE TO RELATED APPLICATIONS

Non-applicable.

BACKGROUND

Generally, when a person has a medical question, they enter a list of symptoms into an internet search engine. This approach results in the person sharing private and sensitive medical information (e.g., a string of symptoms) with online web providers, without any control as to how that information may be used, stored, or disseminated to others. Moreover, the results provided by the search engine may be inaccurate or flat-out incorrect, as the search engine may include false information and fake science. Thus, the person may have revealed private and potentially identifying information and received dubious and/or dangerous medical advice in return.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In embodiments, the messaging service facilitates secure two-way communications between an end user device and a server or internet-based application. Once security is established and user identity is verified, the messaging service can receive and parse user input such as text-based messages and voice-recognized speech, identify contextual information with natural language processing, map parsed data to securely-stored server-side user-specific records and specialized databases (e.g., medical terminology and HL7 workflow transaction messages), and provide a user end device with information that has been customized or personalized in near real-time, such as medical and wellness information that is responsive to the original user input.

BRIEF DESCRIPTION OF THE DRAWINGS

Examples are described in detail below with reference to the attached drawing figures, wherein:

FIG. 4 is an exemplary illustration of programming code that underlies a secure messaging service, in accordance with an embodiment of the present invention;

FIG. 6 is an exemplary illustration of programming code that underlies a secure messaging service, in accordance with an embodiment of the present invention;

FIG. 7 is an exemplary illustration of programming code that underlies a secure messaging service, in accordance with an embodiment of the present invention;

FIG. 10 is an exemplary computer programming code supporting a secure messaging service, in accordance with an embodiment of the present invention;

FIG. 12 depicts exemplary computer programming code supporting a secure messaging service, in accordance with an embodiment of the present invention;

FIG. 17 depicts exemplary computer programming code supporting a secure messaging service, in accordance with an embodiment of the present invention;

DETAILED DESCRIPTION

Figure 1:
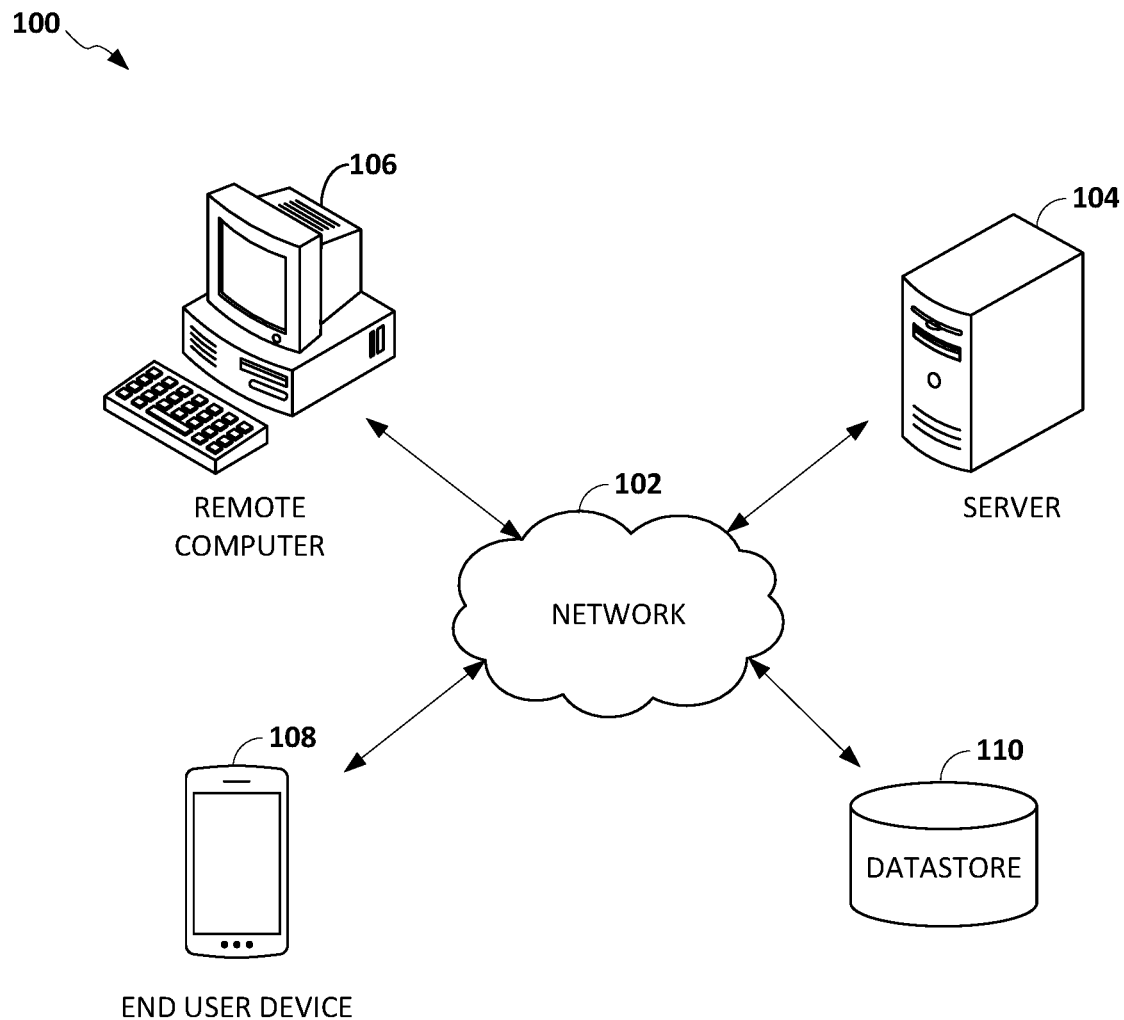
FIG. 1 depicts an exemplary computing environment in accordance with an embodiment of the present invention.

At a high level, the present invention is directed toward an internet-based or application-based messaging service having security features and performing near real-time integration of data that is specifically customized for and responsive to a user.

Generally, embodiments of the invention include the receipt of an indication from a user of a user device that signals the user wishes to interact with a secure messaging service or assistant. The user's identity is verified and an electronic medical record that is specific to user is retrieved. The electronic medical record is securely stored, for example, at a server that facilitates secure two-way communications with the user device throughout the interaction. An image of a human body is generated and displayed at the user device, so that the user may select one or more portions of the human body. The human body that is generated is specific to the gender of the user, as identified by verifying the user's identity. When the user's identity is associated with a female gender, a female human body is displayed, for example. When the user's identity is associated with a male gender, a male human body is displayed. These selections are, generally, user indications of relevant anatomy and/or symptoms to be discussed with the secure messaging service or assistant. The secure messaging service or assistant initiates a messaging interface between the server and the user device, which prompts the user to provide user input. The user conducts a natural language conversation with the secure messaging service or assistant. Again, the two-way communications between the server and the user device are secure (e.g., FHIR and HL7 compliant). As user input is received, the secure messaging assistant parses the user input using natural language processing to identify one or more keywords in near real-time. Keywords may include medical symptoms, for example. The keywords are mapped to medical events in the electronic medical record of the user and to selected image portions (e.g., relevant anatomy). The secure messaging assistant identifies at least one medical condition that is associated with, and determined to be relevant to, the keywords and the medical events. Then, the medical condition is securely communicated to the user device to be displayed to the user.

The invention herein addresses the lack of security involving private information, as generally experienced by persons who employ an internet search engine to obtain medical and wellness information. Securing private information, including potentially user-identifying information, which may need to be communicated over wired and wireless networks, is a technological problem that arose with the Internet itself. Preventing private information from unwanted disclosure to data collecting enterprises, sale to unknown parties and vendors, and exposure or interception by malicious entities, remains a problem that has not been met by existing technologies. Internet-based security is constantly under attack from a barrage of new and evolving malicious hacks and attacks that emerge daily. The majority of a person's device-based interactions with the Internet (e.g., visiting a website, inputting a query and conducting a search on a search engine) and applications of the device (e.g., taking a photo with a mobile device application that collects geographic location, date, and time information) actively collect and share a person's information transparently. The term transparently is used to indicate that a person does not have any knowledge, notification, or indication that their private information is being collected, accessed, or otherwise obtained for sharing with other entities.

The invention improves on existing technology because the claimed embodiment provides internet-based and/or application-based security for private information that is used to obtain medical and wellness information. This prevents the unwanted disclosure to or interception of private and potentially user-identifying information by other parties and entities. Private and potentially user-identifying information is no longer released to an internet search engine or other website (e.g., cookies, history, and malware). The invention achieves these improvements by providing a secured two-way communication internet-based or mobile-device application that includes verification features. The invention also leverages Fast Healthcare Interoperability Resources (FHIR) web-based technologies and Healthcare Level 7 (HL7) application-layer technology.

In addition to addressing the lack of security involving private information and in addition to providing an improvement to existing technology, embodiments of the invention also provide practical benefits. Using the claimed embodiments of the invention discussed hereinafter, persons can easily obtain medical information and wellness information with improved accuracy and without inadvertently sharing private and potentially identifying information.

One embodiment provides a computer-implemented method. The method comprises verifying the identity of a user of the user device and retrieving one or medical events stored in an electronic medical record that is specific to the identity of the user. The electronic medical record being securely stored, generally at a server or database. The method further comprises generating an image of a human body having selectable portions to be displayed via the user device. The method continues by identifying at least one of the plurality of portions when selected from the image when a selection indication is received from the user device. The method further comprises initiating a secure messaging assistant that prompts the user to provide user input. When user input is received via the secure messaging assistant, the method performs parsing the user input using natural language processing to identify one or more keywords and mapping the one or more keywords to the one or more medical events in the electronic medical record and the at least one of the plurality of portions selected from the image. The method further identifies, from the mapping of the one or more keywords, at least one medical condition associated with the one or more keywords and the one or more medical events. The method securely communicates the at least one medical condition to the user device to be displayed to the user.

In another embodiment, one or more non-transitory computer-readable storage media having computer-executable instructions embodied thereon that, when executed, perform a method. The media comprises one or more processors configured to verify the identity of a user of a user device and retrieve medical events in an electronic medical record that is specific to the user, the electronic medical record being securely stored on a server. The one or more processors are further configured to generate an image of a human body to be displayed via the user device, where the image of the human body comprises a plurality of selectable portions when displayed. When a selection is received from the user device, the one or more processors are configured to identify at least one of the plurality of portions of the human body selected from the image. The one or more processors are further configured to initiate a secure messaging assistant that prompts the user to provide user input. Then, when user input is received via the secure messaging assistant, the one or more processors parse the user input using natural language processing to identify one or more keywords and map the one or more keywords to the one or more medical events retrieved and the at least one of the plurality of portions selected from the image. The one or more processors identify, from mapping of the one or more keywords to the one or more medical events, at least one medical condition associated with the one or more keywords and the one or more medical events. The one or more processors are configured to securely communicate the at least one medical condition to the user device to be displayed to the user.

A system is provided in yet another embodiment. The system comprises a database that securely stores electronic medical records including medical histories of a plurality of patients. The system further comprises a server. The server is configured to verify an identity of a user and retrieve one of the electronic medical records that are specific to the identity of the user. The server also provides an image of a human body having selectable portions for display to the user. The server is configured to identify at least one of the selectable portions when selected from the image by the user. The server initiates a secure messaging assistant that prompts the user to provide user input. When user input is received via the secure messaging assistant, the server is configured to parse the user input using natural language processing to identify one or more keywords. The server maps the one or more keywords to one or more medical events in the one electronic medical record and to the at least one of the plurality of portions selected from the image and the server identifies, from the mapping of the one or more keywords, at least one medical condition associated with the one or more keywords and the one or more medical events. The server securely communicates the at least one medical condition to the user device to be displayed to the user.

As used in this Detailed Description, real-time and near real-time refer to a time delay that is typically introduced by data processing itself. Real-time and near real-time processes generally lack purposeful or intentionally added latency. As such, the terms real time and near real time, as used throughout this disclosure, capture time delays introduced by the manipulation of data, for example, receiving, retrieving, referencing, processing, displaying, communicating, transmitting, and/or storing data. The terms real time and near real time are used interchangeably for the purposes of this Detailed Description.

The embodiments of the present invention generally operate in computing system environments. Exemplary computing system environments and configurations thereof that may be suitable for operation of the present invention include, for example, one or more local servers, remote servers, virtual machines run on computing devices such as servers, end user devices, personal computers (PCs), laptop computing devices, mobile user devices such as cell phones, pagers, and tablets, multiprocessor systems, microprocessor-based systems, set-top boxes, programmable consumer electronics, network PCs, minicomputers, mainframe computers, distributed computing environments that include one or more of the above-mentioned computing system environments and configurations and the like.

The present invention may be operational and/or implemented across computing system environments such as a distributed or wireless "cloud" system. Cloud-based computing systems include a model of networked enterprise storage where data is stored in virtualized storage pools. The cloud-based networked enterprise storage may be public, private, or hosted by a third party, in embodiments. In some embodiments, computer programs or software (e.g., applications) are stored in the cloud and executed in the cloud. Generally, computing devices may access the cloud over a wireless network and any information stored in the cloud or computer programs run from the cloud. Accordingly, cloud-based computing system may be distributed across multiple physical locations, for example.

Beginning with FIG. 1, an exemplary computing environment is depicted, in accordance with an embodiment of the present invention. It will be understood by those of ordinary skill in the art that the exemplary computing environment 100 is just one example of a suitable computing environment and is not intended to limit the scope of use or functionality of the present invention. Similarly, the computing environment 100 should not be interpreted as imputing any dependency and/or any requirements with regard to each component and combination(s) of components illustrated in FIG. 1. It will be appreciated by those having ordinary skill in the art that the connections illustrated in FIG. 1 are also exemplary as other methods, hardware, software, and devices for establishing a communications link between the components, devices, systems, and entities, as shown in FIG. 1, may be utilized in implementation of the present invention. Although the connections are depicted using one or more solid lines, it will be understood by those having ordinary skill in the art that the exemplary connections of FIG. 1 may be hardwired or wireless, and may use intermediary components that have been omitted or not included in FIG. 1 for simplicity's sake. As such, the absence of components from FIG. 1 should be not be interpreted as limiting the present invention to exclude additional components and combination(s) of components. Moreover, though devices and components are represented in FIG. 1 as singular devices and components, it will be appreciated that some embodiments may include a plurality of the devices and components such that FIG. 1 should not be considered as limiting the number of a device or component.

Continuing, the computing environment 100 of FIG. 1 is illustrated as being a distributed environment where components and devices may be remote from one another and may perform separate tasks. The components and devices may communicate with one another and may be linked to each other using a network 102. The network 102 may include wireless and/or physical (e.g., hardwired) connections. Exemplary networks include a telecommunications network of a service provider or carrier, Wide Area Network (WAN), a Local Area Network (LAN), a Wireless Local Area Network (WLAN), a cellular telecommunications network, a Wi-Fi network, a short range wireless network, a Wireless Metropolitan Area Network (WMAN), a Bluetooth® capable network, a fiber optic network, or a combination thereof. The network 102, generally, provides the components and devices access to the Internet and web-based applications.

The computing environment 100 comprises a computing device in the form of a server 104. Although illustrated as one component in FIG. 1, the present invention may utilize a plurality of local servers and/or remote servers in the computing environment 100. The server 104 may include components such as a processing unit, internal system memory, and a suitable system bus for coupling to various components, including a database or database cluster. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 104 may include or may have access to computer-readable media. Computer-readable media can be any available media that may be accessed by server 104, and includes volatile and nonvolatile media, as well as removable and non-removable media. By way of example, and not limitation, computer-readable media may include computer storage media and communication media. Computer storage media may include, without limitation, volatile and non-volatile media, as well as removable and non-removable media, implemented in any method or technology for storage of information, such as computer-readable instructions, data structures, program modules, or other data. In this regard, computer storage media may include, but is not limited to, Random Access Memory (RAM), Read-Only Memory (ROM), Electrically Erasable Programmable Read-Only Memory (EEPROM), flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 104. Computer storage media does not comprise signals per se.

Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, radio frequency (RF), infrared, and other wireless media. Combinations of any of the above also may be included within the scope of computer-readable media.

In embodiments, the server 104 is compatible and compliant with FHIR and HL7 protocols. In embodiments, the server 104 uses logical connections to communicate with a remote computer 106 within the computing environment 100. In embodiments where the network 102 includes a wireless network, the server 104 may employ a modem to establish communications with the Internet, the server 104 may connect to the Internet using Wi-Fi or wireless access points, or the server may use a wireless network adapter to access the Internet. The server 104 engages in two-way communication with any or all of the components and devices illustrated in FIG. 1, using the network 102. Accordingly, the server 104 may send data to and receive data from the remote computer 106 over the network 102.

Although illustrated as a single device, the remote computer 106 may include multiple computing devices. In an embodiment having a distributed network, the remote computer 106 may be located at one or more different geographic locations. In an embodiment where the remote computer 106 is a plurality of computing devices, each of the plurality of computing devices may be located across various locations such as buildings in a campus, medical and research facilities at a medical complex, offices or "branches" of a banking/credit entity, or may be mobile devices that are wearable or carried by personnel, or attached to vehicles or trackable items in a warehouse, for example.

In some embodiments, the remote computer 106 is physically located in a medical setting such as, for example, a laboratory, inpatient room, an outpatient room, a hospital, a medical vehicle, a veterinary environment, an ambulatory setting, a medical billing office, a financial or administrative office, hospital administration setting, an in-home medical care environment, and/or medical professionals' offices. By way of example, a medical professional may include physicians; medical specialists such as surgeons, radiologists, cardiologists, and oncologists; emergency medical technicians; physicians' assistants; nurse practitioners; nurses; nurses' aides; pharmacists; dieticians; microbiologists; laboratory experts; genetic counselors; researchers; veterinarians; students; and the like. In other embodiments, the remote computer 106 may be physically located in a non-medical setting, such as a packing and shipping facility or deployed within a fleet of delivery or courier vehicles.

The remote computer 106 may be an end user device 108, such as a mobile device or a handheld device, in embodiments. The remote computer 106 may also include, incorporate, and/or be coupled to additional devices, adapter, or components that provide additional functionality to the remote computer 106. Examples of additional devices include a user-wearable electronic identification device such as a badge or bracelet, an optical scanning device, a radio frequency identification (RFID) reading devices, or a real-time locating system (RTLS) devices. Additionally, the end user device 108 may include or have the same or similar capabilities as an optical scanning device, a radio frequency identification (RFID) reading devices, or a real-time locating system (RTLS) device, in embodiments. For example, the end user device 108 may be a "smart" mobile phone that has a high-definition camera and software applications providing optical scanning functions. In embodiments, the remote computer 106 and/or the end user device 108 may be, or may include, personal computers (PCs), personal digital assistants, tablet devices, personal devices having physiological measuring instruments (e.g., an insulin meter, a "smart" watch, a pacemaker), pagers, servers, routers, peer devices, network nodes, gateways, or the like.

Continuing, the computing environment 100 includes a data store 110. Although shown as a single component, the data store 110 may be implemented using multiple data stores that are communicatively coupled to one another, independent of the geographic or physical location of a memory device. Exemplary data stores may store data in the form of electronic records, for example, electronic medical records of patients, transaction records, billing records, task and workflow records, chronological event records, and the like. In embodiments, the data store 110 is configured to store entity-specific records, each record being specific to one entity or a group of related entities. For example, each one of the electronic records may correspond to one different person, such as a patient or a physician. In embodiments, the data store 110 is compatible and compliant with FHIR and HL7 protocols. The data store 110 securely stores records.

Generally, the data store 110 includes physical memory that is configured to store information encoded in data. For example, the data store 110 may provide storage for computer-readable instructions, computer-executable instructions, data structures, data arrays, computer programs, applications, and other data that supports the functions and action to be undertaken using the computing environment 100 and components shown in exemplary FIG. 1.

In a computing environment having distributed components that are communicatively coupled via the network 102, program modules may be located in local and/or remote computer storage media including, for example only, memory storage devices. Embodiments of the present invention may be described in the context of computer-executable instructions, such as program modules, being executed by a computing device. Program modules may include, but are not limited to, routines, programs, objects, components, and data structures that perform particular tasks or implement particular abstract data types. In embodiments, the server 104 may access, retrieve, communicate, receive, and update information stored in the data store 110, including program modules. Accordingly, the server 104 may execute, using a processor, computer instructions stored in the data store 110 in order to perform embodiments described herein.

Although internal components of the devices in FIG. 1, such as the server 104, are not illustrated, those of ordinary skill in the art will appreciate that internal components and their interconnection are present in the devices of FIG. 1. Accordingly, additional details concerning the internal construction device are not further disclosed herein.

Figure 2:
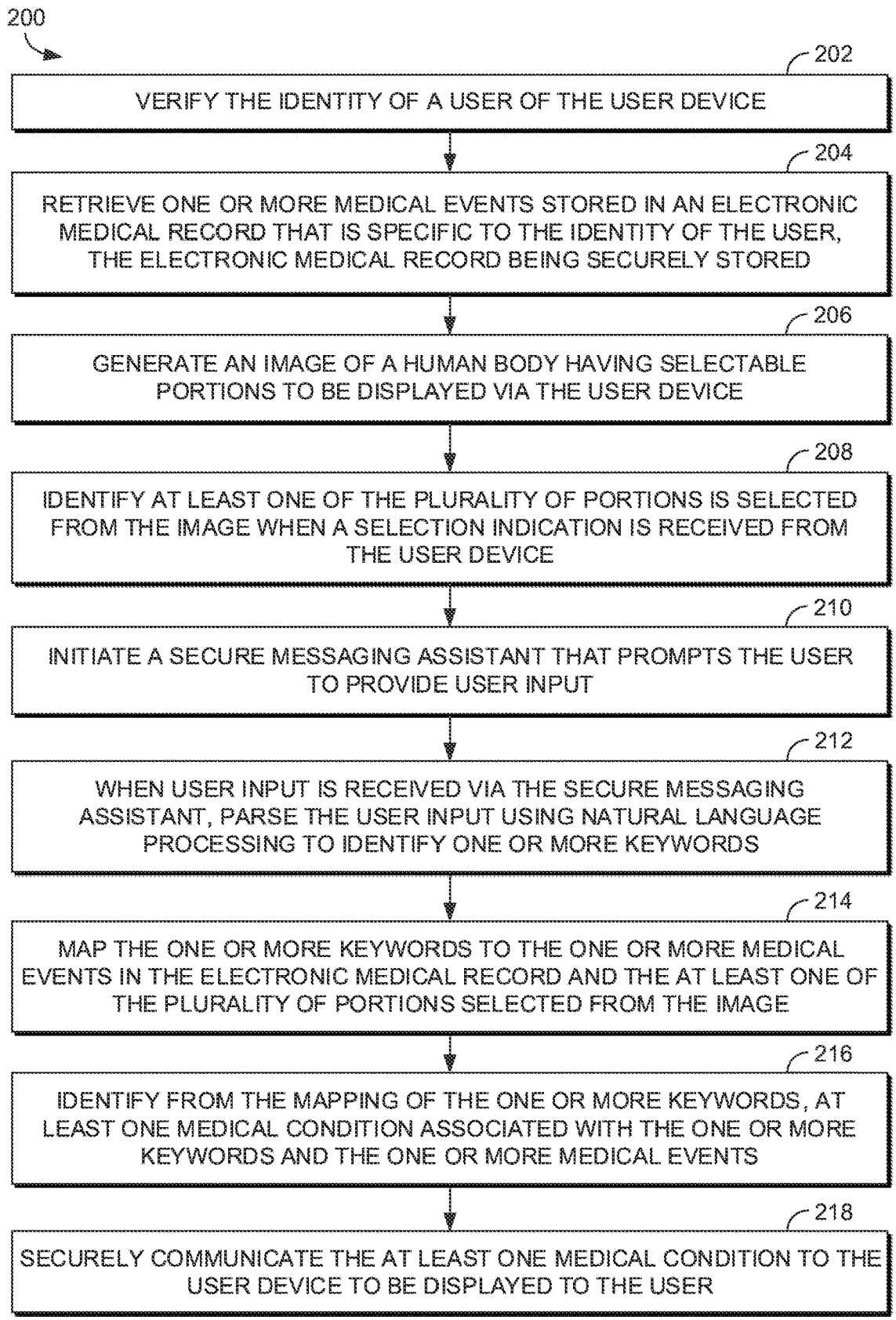
FIG. 2 depicts an exemplary method in accordance with an embodiment of the present invention.

Turning to FIG. 2, an overview of an exemplary computer-implemented method 200 is shown, in accordance with embodiments of the invention. The method 200 provides internet-based and application-based security for private information that is used to obtain medical and wellness information. Generally, the method 200 prevents the unwanted disclosure to or interception of private and potentially user-identifying information by other parties and entities because private and potentially user-identifying information is no longer released to an internet search engine or other website (e.g., cookies, history, and malware). These improvements are achieved as the method 200 is performed to provide secured two-way communication internet-based or mobile-device application that includes verification features.

Figure 3:
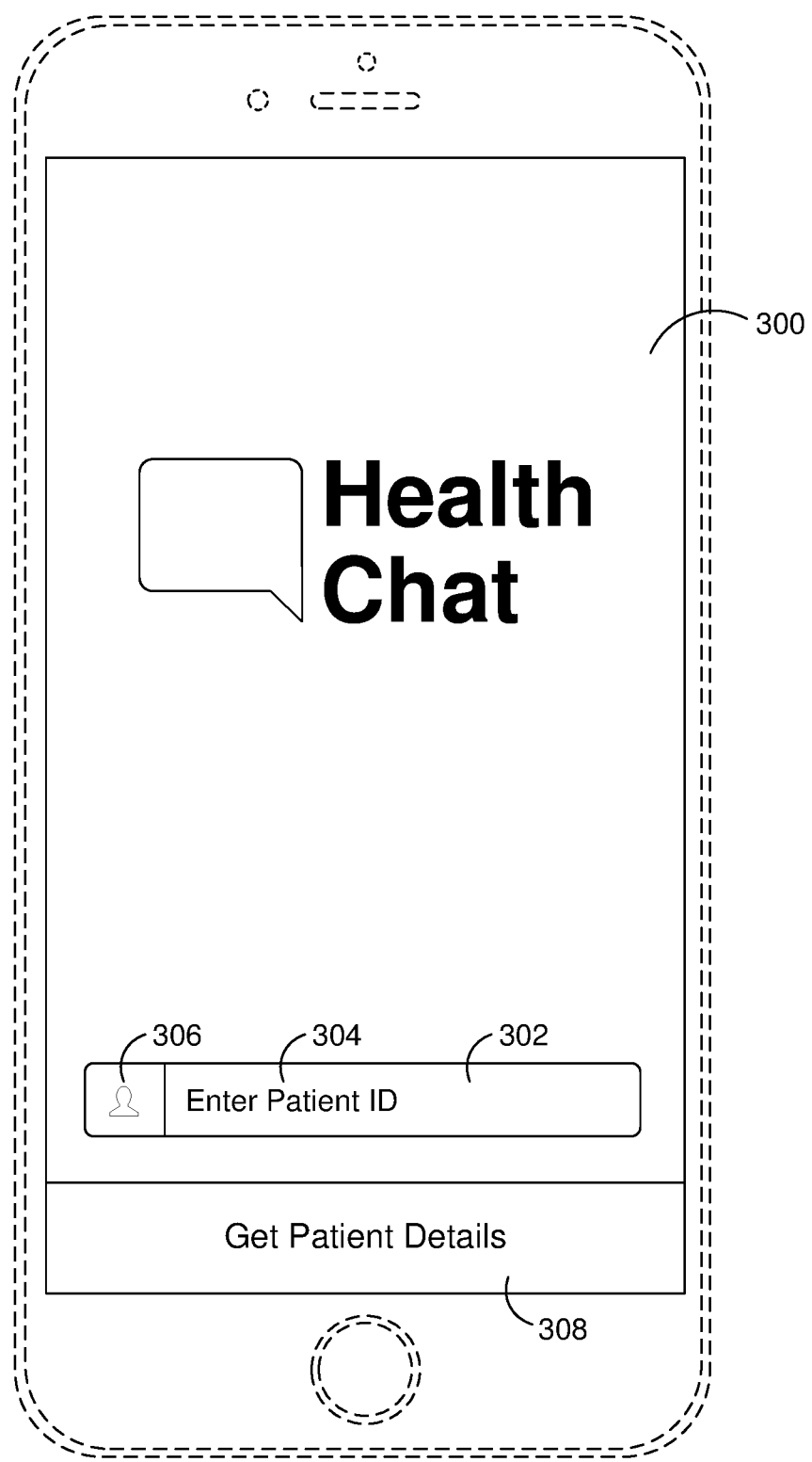
FIG. 3 is an exemplary illustration of a graphical user interface of a secure messaging service, in accordance with an embodiment of the present invention.

In accordance with the method 200 of FIG. 2, a user device accesses an internet-based application or a locally executed application that provides an interface between the user device and a secure server. The application enables the user to securely provide private and potentially user-identifying information and to obtain accurate medical and wellness information. For example, a user device may display a graphical user interface (GUI) "start screen" for the application. FIG. 3 illustrates an exemplary application start GUI 300 for interfacing with a secure messaging service, in accordance with an embodiment of the present invention. The internet-based application or a locally executed application may include one or more prompts that solicit a user to enter an identifier. For example, the application start GUI 300 includes a GUI object that is a text box 302 configured to receive alphanumeric characters or words entered by a user, for example, via an external keyboard, an onscreen keyboard, and/or spoken by a user into a microphone of the user device. The text box 302 includes a message that prompts a user to input an identifier, as the words Enter Patient ID" 304 are displayed within the text box 302 to further indicate a location in the application start GUI 300 for the user to input an identifier. Pictographs and icons may be located adjacent to the text box 302 and act as a signal to a user. For example, exemplary icon 306 presents an outline representing a human head, neck and shoulders which signals to the user that an identifier corresponding to a person, such as the user, should be input to the text box 302. Accordingly, an identifier is input via the user device so that a user may conveniently access a secure messaging service via the application, independent of the user's physical, geographic location.

Alternatively, in some embodiments, a user may enter an identifier using another device (e.g., RFID emitting chip, a security token including an encrypted key) that includes a machine-readable or machine-recognizable code or pin that may be sensed or wirelessly detected by the user device. For example, an RFID tagged patient bracelet is attached to a user upon their admission to a medical center so that the user may place the bracelet in proximity (e.g., less than or equal to 1 meter) to the user device so that the user device detects the RFID tag, which includes an identifier that is unique to the user. Having obtained the identifier, the user device provides the identifier to the application. The identifier may be linked to one electronic record for the duration of the user's admission at the medical center, for example.

In some embodiments, a server or an application in communication with a server sends a request to the user device that requests the identifier be input to the user device. In one embodiment, when an indication is received by the server, for example, that the user device is initiating or has initiated an application for launching a secure messaging service, a request for an identifier is communicated to the user device from the server.

An identifier is unique to one user. Exemplary identifiers include a patient identification number, a medical records number, a Social Security Number, a birthdate, and residential address of a user, an Internet Protocol (IP) address of the user device, a pin number, a password, a gesture password (e.g., entered with a touchscreen), a sequence or string of alphanumeric characters and/or symbols, and the like. The identifier may be assigned to the user by a medical professional and/or a medical facility. The identifier may be assigned to the user by a government entity, such as a national health service. Identifier may not include any identifying information, such as a name, but rather maybe a random sequence of numbers letters or symbols. In some embodiments, a unique identifier is automatically and randomly generated, for the user, each time the secure messaging service is accessed by the user device.

Generally, the identifier is an alphanumeric sequence that can be easily input to a user device, that does not identify the user on its face, that cannot be easily guessed by persons, and/or that cannot easily be deduced (e.g., "cracked") or intercepted using software. In some embodiments, the identifier includes a biometric identifier, such as a fingerprint that can be input to a touchscreen or a spoken passphrase that can be input via a microphone and quickly recognized with speech analysis. In some embodiments, multiple identifiers may be input or required to be input in order to bolster security of the secure messaging service. In some embodiments, the identifier may also be uniquely associated with a user device that is associated with the user.

The identifier is securely communicated to a server. A user may interact with the application start GUI 300 by touching a displayed GUI object in order to trigger the user device and/or the application to securely communicate the identifier to the server. The exemplary portion of computer programming code shown in FIG. 4 supports the underlying functions of the exemplary Get Patient Details GUI button 408, in embodiments. The identifier may be used to identify and/or recognize a user of the user device, for example. Once an identifier is input via the user device, the identifier may be encrypted and communicated to a server performing or facilitating the method 200 of FIG. 2.

Before private and potentially user-identifying information is communicated between the user device and the server, the identity of the user is determined and the user's identity is verified, as explained below. Verifying the identity of the user is just one of the mechanisms utilized to ensure that private and potentially user-identifying information is not disclosed or released to an internet search engine or third parties, for example.

When an identifier is received, the server searches a database and locates an electronic medical record that is specific to the identity of the user. The electronic medical record is securely stored on in a database that is communicatively coupled to the server. The identifier may be used to search for records and information that are specific to the identifier, which are therefore specific to the user. The identifier may act as a query which can be searched within a plurality of records stored securely in the database. Generally, the identifier may be used to locate an electronic record that is specific to the identity of the user, such as an electronic medical record. In further embodiments, the identifier is matched to an entry in a data index that stores a secondary user identifier, and the secondary user identifier is used to locate the electronic record that is unique to the identity of the user. This may provide an additional layer of security, as interception of the identifier alone would not compromise the private information securely stored elsewhere (e.g., the data index would also need to be breached for a malicious entity to locate the secondary identifier, without which a matching electronic record cannot be identified). This extra layer of security may also be useful in systems that utilized a cycling security token as an identifier. The identifier (e.g., or secondary identifier) that corresponds to the user of the user device is used as a query to search, locate, and identify an electronic medical record that is specific to the user, in embodiments.

Figure 5:
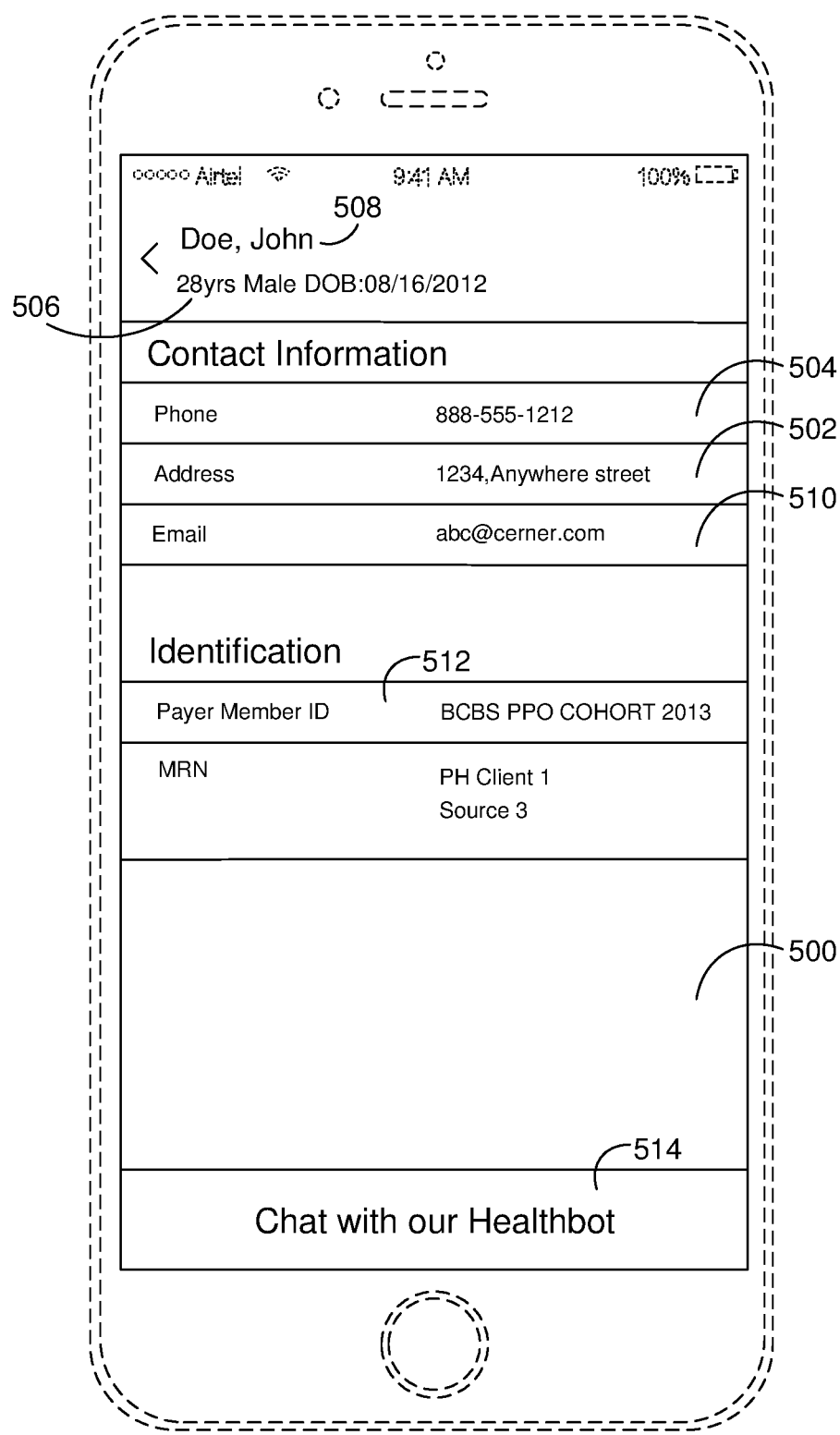
FIG. 5 is an exemplary illustration of a graphical user interface of a secure messaging service, in accordance with an embodiment of the present invention.

Having found the electronic record that corresponds to the user of the user device, based on the identifier, verification may be performed by the server and/or by the user of the user device. The method 200 includes verifying the identity of the user of the user device, as shown at block 202. In embodiments, at least some of the information from the user-specific medical electronic record is retrieved by the server and is displayed at the user device, as shown in the verification GUI 400 of exemplary FIG. 5. The verification GUI 500 allows a user to visually inspect the retrieved information and confirm whether the information displayed at the user device is accurate and correct. The information that is retrieved by the server and displayed at the user device may be selectively chosen. In other words, basic information such as that shown in the verification GUI 500 of an address 502, phone number 504, age 506, and name 508 may be presented while more private or compromising information such as a medical diagnosis or weight is not shown. Additional information may be presented such as an email 510 and health plan information 512 that are specific to the user and the corresponding identifier. The information presented in the verification GUI 500 is selectively chosen to be benign, which would avoid embarrassment and avoid accidental disclosure of sensitive or embarrassing medical information to the incorrect user, for example. Thus, if the wrong electronic record was retrieved somehow, a user could indicate the error, via the verification GUI 500 at the user device, without the server and application erroneously providing physical descriptions, medical diagnosis, and the like to the wrong user. Information such as an address, phone number, age, and name is usually benign if accidently presented.

A user may confirm that the information displayed is accurate and correct by entering user input (e.g., using a touch screen to tap) to select a GUI object (e.g., button, check box) that indicates the user is confirming their identity. A user may verify that the information displayed is accurate and correct by entering user input (e.g., using a gesture on the user device) to select a GUI object, which indicates that the user wishes to proceed with the method 200 for the secure messaging service. For example, a user may touch a touchscreen of the user device to select a GUI object (e.g., Chat with our Healthbot GUI button 514) to continue to the secure messaging features provided by the server, via the application. FIG. 6 illustrates exemplary portion of computer programming code that supports the method in this regard.

When the user's identity verified, the method 200 includes retrieving the user-specific electronic medical record. For example, FIG. 7 provides exemplary portion of computer programming code that supports the method in this regard. As shown at block 204, one or more medical events stored securely in the electronic medical record that is specific to the identity of the user are retrieved. The server, for example, scans or parses the electronic medical record to identify one or more medical events documented in the user-specific electronic medical record. The server may also use image analysis and/or image tags to identity medical images, for example, stored in user-specific electronic medical record. The medical events are automatically identified. The electronic record and the identified medical events may be securely cached at the server, in some embodiments. The electronic record and the identified medical events may be held in temporary memory or transient memory at the server, in embodiments. The cache memory or temporary memory may be assigned to the user device and configure to support the current initiation of the application for the secure messaging service, in some embodiments. Cache memory and temporary memory, generally, is erased, purged, or overwritten when the current instantiation of the application for the secure messaging service is terminated, after a predetermined period of time (e.g., a timeout), or when a communication connection between the user device and the server is interrupted. As such, the electronic record and the identified medical events are held at the server for a limited period time, which reduces the risk of information theft by third parties and malicious entities.

Medical events include documented items in a chronological medical history of the user such as visits with a medical professional, past or scheduled treatments and procedures (e.g., inpatient and outpatient surgery), past or current diagnosis and medical conditions, past or current drug prescriptions, pathology and lab testing results, inoculations, notes entered by medical professionals, and the like. The identified medical events also include demographic information of the user such as age, age group, gender, race, ethnicity, religion, location, address, city, zip code, income range, profession, medical insurance provider, medical insurance plan, and travel history (e.g., possible exposure to tropical maladies), for example. The identified medical events may also include, for example, genetic testing results, family medical histories, diagnosis and medical conditions of relatives (e.g., blood-related or co-habiting relatives), a designation of degree of a familial relationship to the user (e.g., maternal grandmother, father, brother, half-sister, paternal uncle, first cousin, nephew, daughter), and the like.

Figure 8:
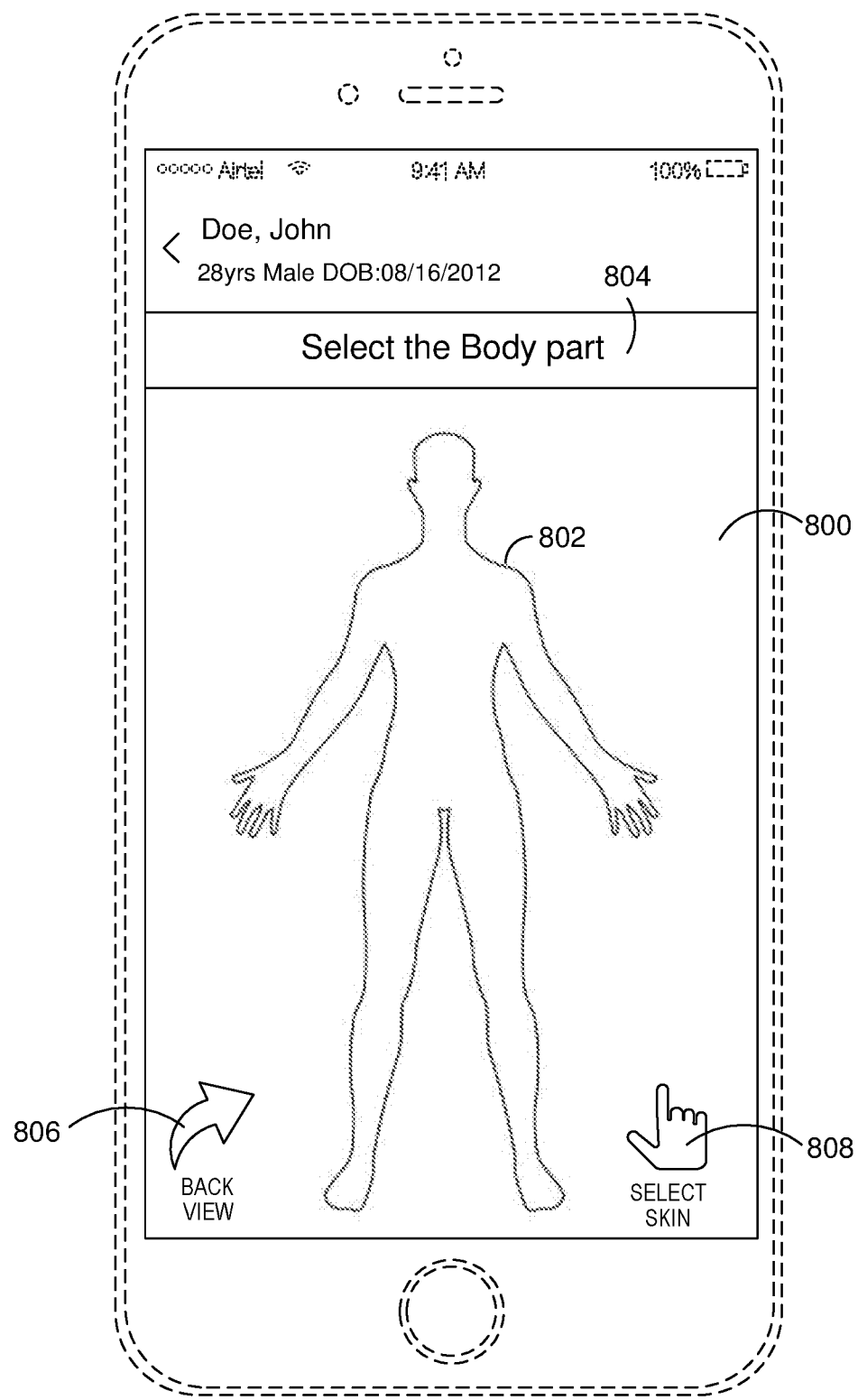
FIG. 8 is an exemplary illustration of a graphical user interface of a secure messaging service, in accordance with an embodiment of the present invention.

During retrieval or after retrieval of the electronic record including the user's demographics and the user's family medical histories, for example, the method 200 includes generating an image of a human body having selectable portions to be displayed via the user device, shown at block 206. In an embodiment, the server generates the image and communicates the image to the user device, where the image is displayed to a user in the application. The server may instruct the application to generate the image, in some embodiments. In one example, the image GUI 800 of FIG. 8 includes an image that is a simplified outline of a human body form 802. The user may be prompted to interact with the image GUI 800 when a message is displayed such as 804 Select The Body Part. In accordance with the method 200, the image of the human may include a whole body form, in some aspects. An image of human body is a visual or pictorial representation of limbs, torso, head, and extremities, for example. Exemplary images of a human body include a representation of, at least, the main features of a human body. Different levels of simplicity or detail may be included in the image. For example, the image of the human body may be a two-dimensional representation that is an outline of a human body. The image of the human body may include facial features such as eyes, a mouth, and a nose. The image may be depicted similar to an anatomical illustration, a virtual reality avatar, or exhibit a photograph-like appearance, in various embodiments.

Generally, the image is a user interactive image. A user interactive image is a visual representation for presentation via GUI, where that image includes features in addition to the visual image itself. The interactive features are activated by user input and/or are responsive to user input, for example, received via a user device. User input may include a user touching a touchscreen with a tap, a gesture, a press-and-hold, for example. The image may include one or more portions, each of which may be interactive. As such, an arm portion of the image of the human body may be interactive and selectable via user input, for example. The head portion of the image of the human may also be interactive and separately, or concurrently, selectable. As such, a user may select one or more portions of the human body by interacting with the image on the user device.

In some embodiments, the image of the human body may be interacted with to produce more than one view of the human body. For example, the image may be rotated in order to present an anterior view (e.g., ventral, front), posterior view (e.g., dorsal, back), and lateral views (sides) of the human body in the image. As shown in exemplary FIG. 8, a user may view the back of the human body by making a selection at or near the "Back View" GUI object 806 as displayed on the image GUI 800. The "Back View" GUI object 806 provides for manipulating the human body form 802 displayed via the image GUI 800. The image of the human body may be rotated about the craniocaudal axis of the human body, for example. The image may be toggled such that a user may input gestures, taps, clicks, and the like to reduce or enlarge one or more portions of the image of the human body. This enables, for example, the user to zoom-in or zoom-out of image of the human body.

The image of the human body may also be customizable for a user or population. For example, a user may be able to select a preferred skin tone for the image of the human body. The level of detail presented in the image of the human body may be customizable as well, as some populations may find, from a cultural stance, that a hyper-realistic representation of the human body is obscene or unnecessary. In one embodiment, the level of detail may be increased such that as detail is increased, the number of selectable portions of the image increases as well. For example, if the level of detail is increased to so that the image includes a representation of joints in the limbs, portions of the images of the human body that correspond to the joints may become selectable. The user may also indicate that they wish to select the skin organ using a "Select Skin" GUI object 808 as shown in the image GUI 800.

Any selections of the human body are securely communicated from the user device to the server, as these selections represent private and potentially user-identifying information. Thus, rather than the user opting to use an unsecured search engine to query medical problems associated with a particular part of their body, the application and server are enabling a secure two-way communication of the user's input, including selections within the image of the human body. This security for the private user input may be especially important when the user is concerned with medical conditions, symptoms, and areas of the human body that are associated with privacy or may be associated with stigma.

In embodiments, a user selects one or more portions of the human body, using the image in the application. In accordance with the method 200, when a selection indication is received from the user device, at least one of the plurality of portions that is selected from the image of the human body is identified (block 208).

Figure 9:
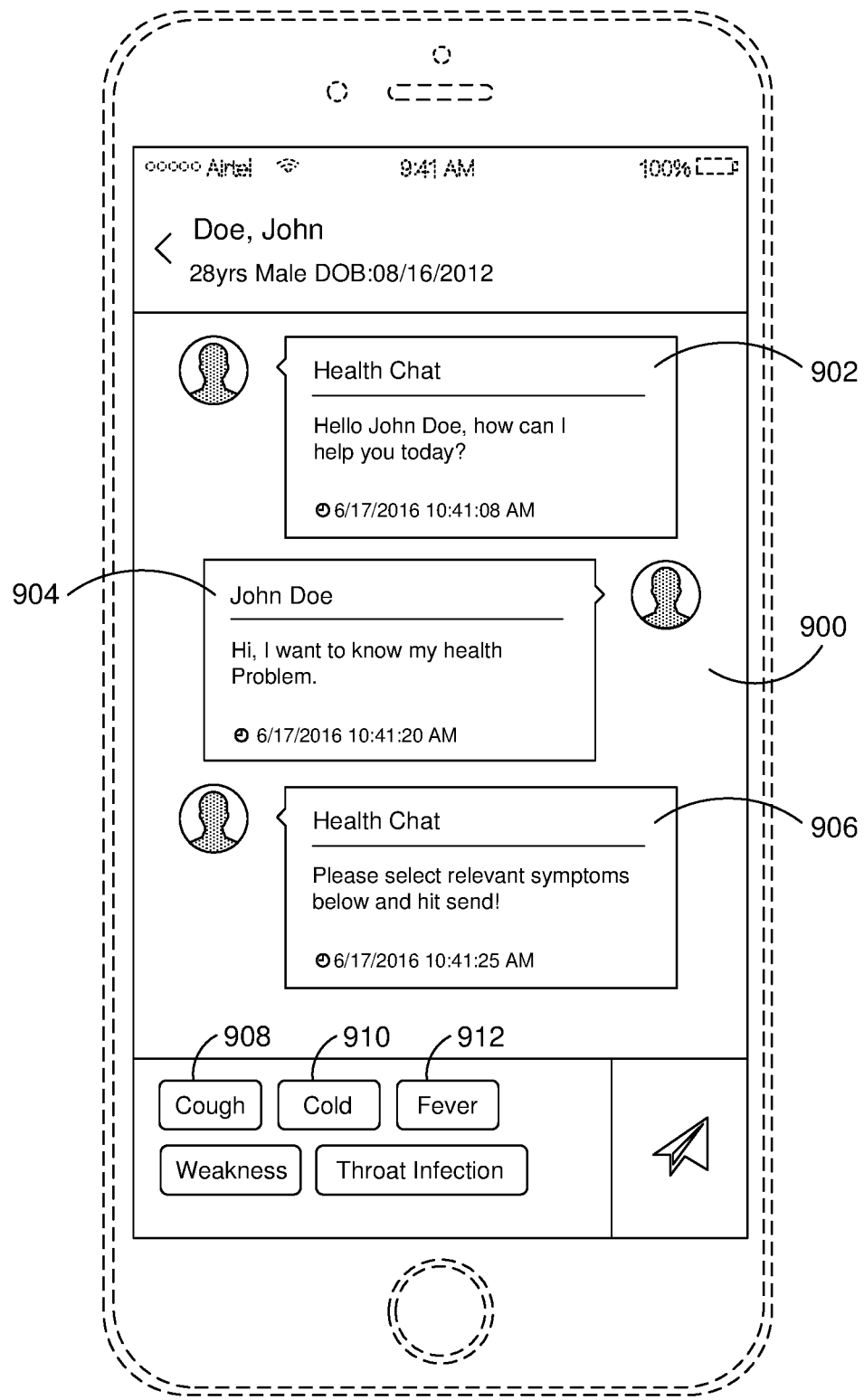
FIG. 9 is an exemplary illustration of a graphical user interface of a secure messaging service, in accordance with an embodiment of the present invention

The method 200 continues by initiating a secure messaging assistant that prompts the user to provide user input, as shown at block 210. In embodiments, the secure messaging assistant is compatible with FHIR and HL7 protocols. The secure messaging assistant facilitates a natural conversation with the user. For example, the messaging GUI 900 of FIG. 9 illustrates an initiated secure messaging assistant that presents a message customized for the verified user (e.g., "Hello John Doe, how can I help you today?" 902) to facilitate a personal and welcoming interaction. The user and the secure messaging assistant may therefore engage in a natural conversation. The secure messaging assistant enables a user to enter text-based user input or voice user input, and can reply to conduct a conversation with the user. The terms "secure messaging service" and "secure messaging assistant" are used interchangeably herein. As shown in exemplary messaging GUI 900, John Doe may input a sentence 904 such as "Hi, I want to know my health problem" as an interaction with the securer messaging service. FIG. 10 provides an exemplary portion of computer programming code that supports the method 200 and GUI 900 in this regard.

Figure 11:
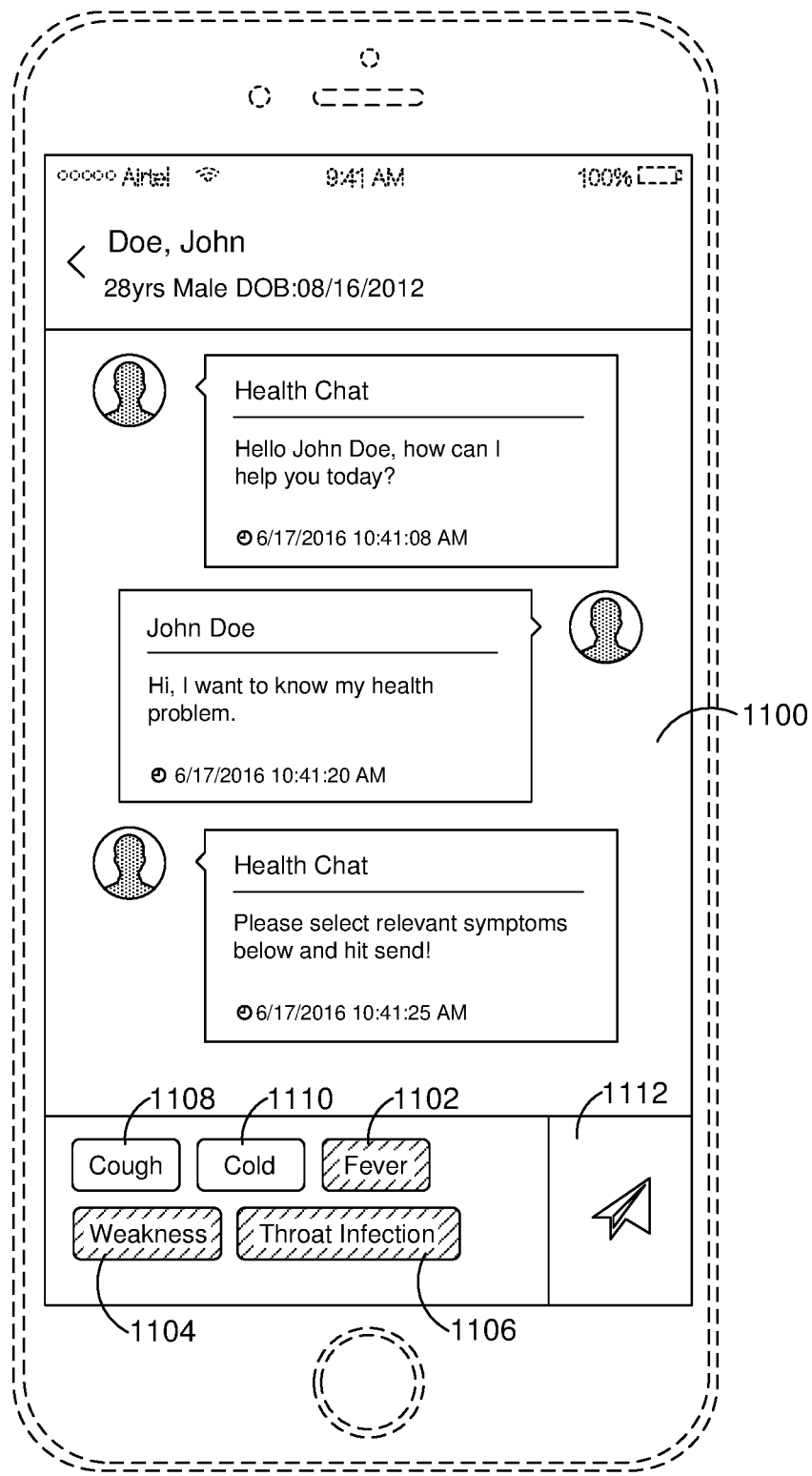
FIG. 11 is an exemplary illustration of a graphical user interface of a secure messaging service, in accordance with an embodiment of the present invention.

The method 200 may prompt a user of the user device to provide additional user input via the secure messaging assistant, in some embodiments. For example, the secure messaging assistant may ask the user for user input by providing a question or message to the user via text on the GUI or by audio playback through a speaker of the user device, for example. Prompting of a user to input information may include displaying a text message (e.g., Please select the relevant symptoms . . . 906) and/or one or more suggested keywords (e.g., Cough 908, Cold 910, Fever 912) via the user device, as shown in the messaging GUI 900 of FIG. 9. Looking to the user-specific electronic medical record, the identified medical event(s), and the selected portion(s) of the image, the secure messaging assistant may provide suggested medical symptoms as keywords, which are considered relevant to the user, based on machine-learning techniques. These keywords may be interactive such that a user may touch a touchscreen of the user device to select one or more of the suggest keywords. For example, the user may determine that some of the suggested keywords are relevant to the conversation with the secure messaging assistant because the user is experiencing medical symptoms that correspond to those keywords. For example, the keyword selection GUI 1100 of FIG. 11 provides visual feedback to a user that indicates to the user positive selection of GUI objects that represent keywords (e.g., Fever 1102, Weakness 1104, Throat Infection 1106 are selected). Visual feedback is provided so that selected GUI object are visually distinguishable from unselected GUI objects, such as the exemplary keywords presented on GUI objects Cough 1108 and Cold 1110. Suggested keywords may be past or current medical diagnosis, conditions, or symptoms that are tagged or parsed from the user-specific electronic medical record, for example. A user may select a GUI object (e.g., send icon GUI button 11112) to indicate the user has finished making selections of keywords, in embodiments. FIG. 12 presents an exemplary portion of computer programming code that supports the method 200 in this regard.

Keywords may be predetermined words that the method 200 and systems herein utilize for natural language processing and mapping, as described below. Keywords may be stored at the server, for example, in structured data such as an index or node map, which may be used to recognize keywords or portions of keywords within user input. The keywords may be stored as associated with one or more of a medical diagnosis, other symptoms, and diagnostic criteria for medical conditions.

In an alternative embodiment, each selection of a keyword may trigger the presentation of a new keyword on the GUI. The new keyword may be relevant to the selected keyword. In such an embodiment, computer-learning examines the user-specific electronic medical record, selected image portion(s) of the body, selected keyword(s), as well as unselected keyword(s) and refines the keywords that were displayed to the user by providing the user with more keywords of increased relevancy and specificity for user selection. Each selected keyword provides positive feedback and each unselected keyword provides a negative inference that is used, ultimately, to provide medical and wellness information that is responsive to all of the user input.

User input is received and may include one or more user-selected keywords, user-input text, speech, other audio recordings (e.g., a cough or wheezing breathing recorded at the user device), and/or images (e.g., a photo of a skin rash taken with a camera at the user device), for example. When user input is received via the secure messaging assistant, the user input is parsed using natural language processing to identify one or more keywords, in accordance with the method 200 at block 212. Speech recognition analysis maybe performed to identify one or more keywords present in voice recording, in embodiments. Keywords may be used to tag label audio recordings (e.g., a user selected keyword Cough may be used to tag user-provided audio data) or images (e.g., a keyword Rash may be used to tag or label user-provided image data based on a selectable portion of the image that corresponds to skin). In one example, when the user input via the secure messaging assistant includes audio data, a speech recognition analysis is performed on the audio data in order to determine determining whether the audio data includes a keyword. If so, the audio data may be tagged with the keyword, tagging the audio data with the keyword. In further embodiments, the audio data may also be stored as a new entry in the electronic medical record that is specific to the user.

Keywords may be extracted from user input for additional processing. Generally, keywords are or correspond to symptoms that the user is experiencing or otherwise reporting to the secure messaging service. Using natural language processing, the user input is parsed to reveal and recognize the syntax and syntactic arrangements that may be present in the user input. The parsing of user input is performed in real or near real-time, relative to the receipt of the user input. In some aspects, the keywords (e.g., symptoms) are extracted and used as queries against a user-specific electronic medical record, a medical dictionary, and/or a database storing medical conditions (e.g., medical encyclopedia and/or differential diagnosis workflows).

Figure 13:
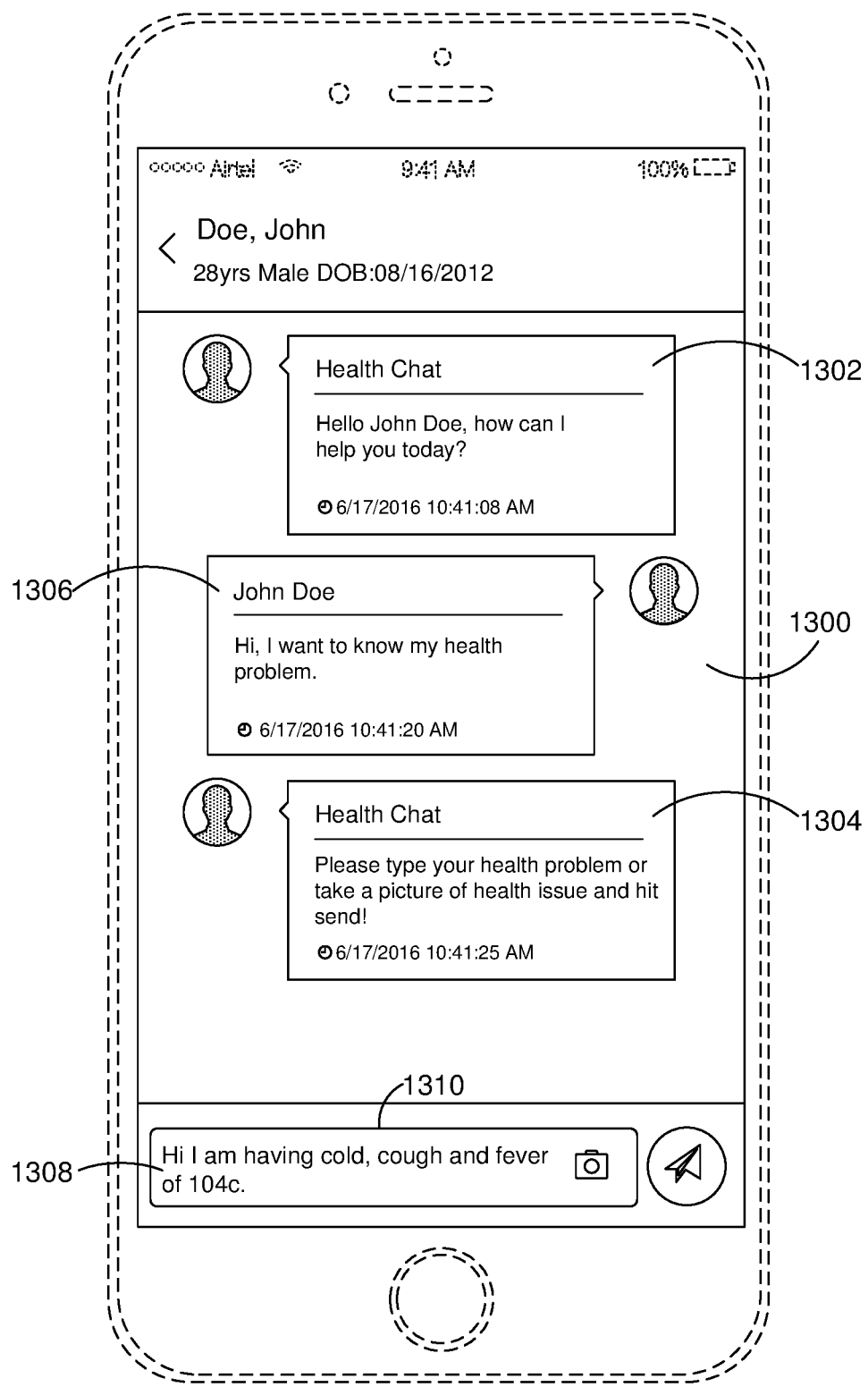
FIG. 13 is an exemplary illustration of a graphical user interface of a secure messaging service, in accordance with an embodiment of the present invention.
Figure 14:
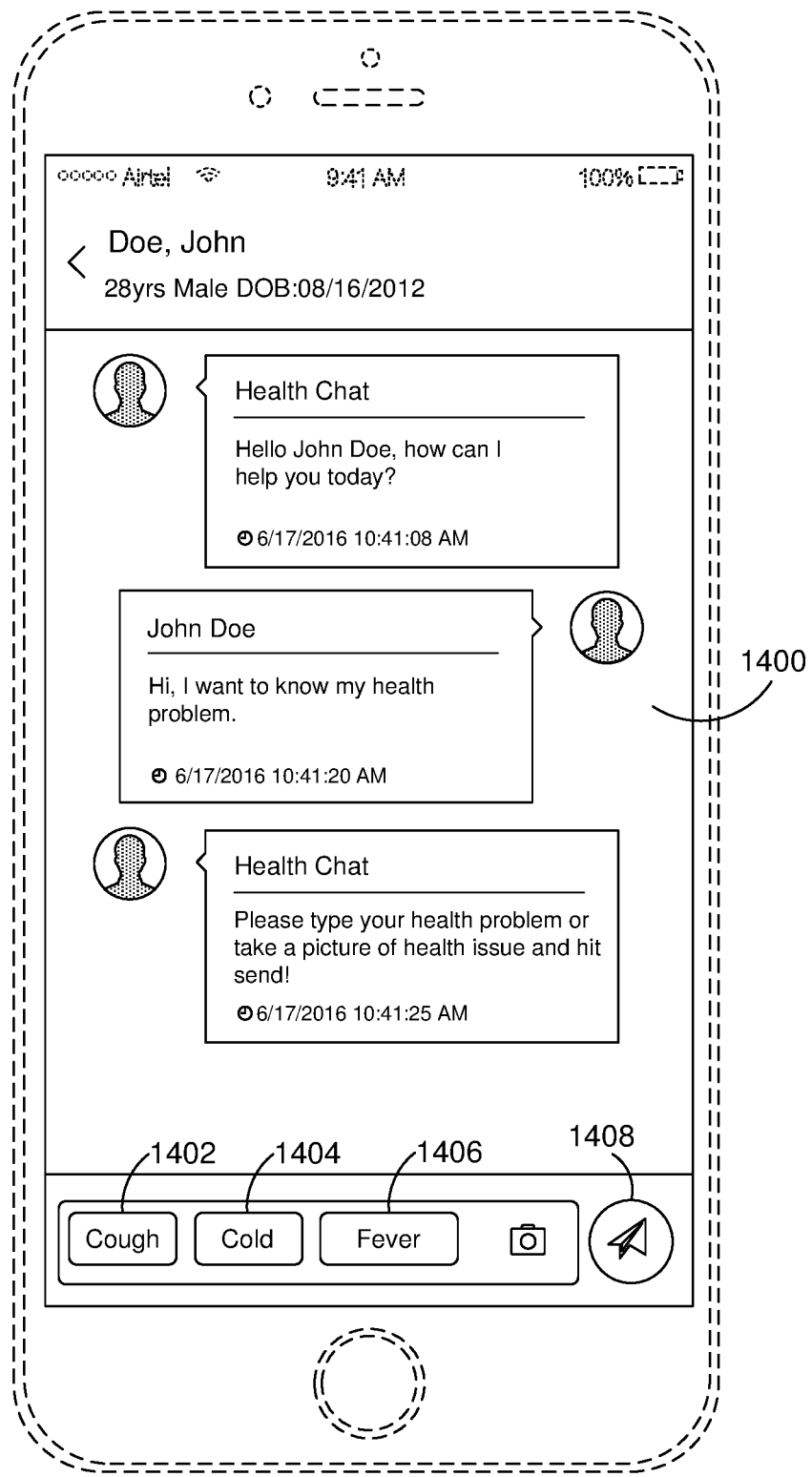
FIG. 14 is an exemplary illustration of a graphical user interface of a secure messaging service, in accordance with an embodiment of the present invention.

Additionally or alternatively, a user may provide input as text, including a greeting with complete or partial sentences, for example, as shown in the messaging GUI 1300 of FIG. 13. In this way, the secure messaging service is conducting a natural conversation using text 1302, 1304 and receiving input 1306, 1308 from a user. The user may input text, for example, into a GUI field 1310 that is configured to receive text input, as shown in the messaging GUI 1300. The text may include alphanumeric characters, symbols, or even emoji (i.e., pictograph), for example. The secure messaging service parses the text of the natural conversion to identity symptoms and extract those symptoms as keywords. These identified symptoms may be presented via a messaging GUI 1400, as shown in FIG. 14 to provide visual feedback to the user or to act as a confirmation that the text has been received. An example of visual feedback includes symptoms like Cough 1402, Cold 1404, Fever 1406 as shown in the exemplary messaging GUI 1400 of FIG. 14. In one embodiment, the secure messaging service parses the language to identity symptoms and extracts those symptoms as keywords as the user inputs the text, in near real-time. In another embodiment, the secure messaging service parses the language to identity symptoms and extracts those symptoms as keywords after the user has input text and activated a function to send the text to the secure messaging service (e.g., GUI object that is button 1408).

Figure 15:
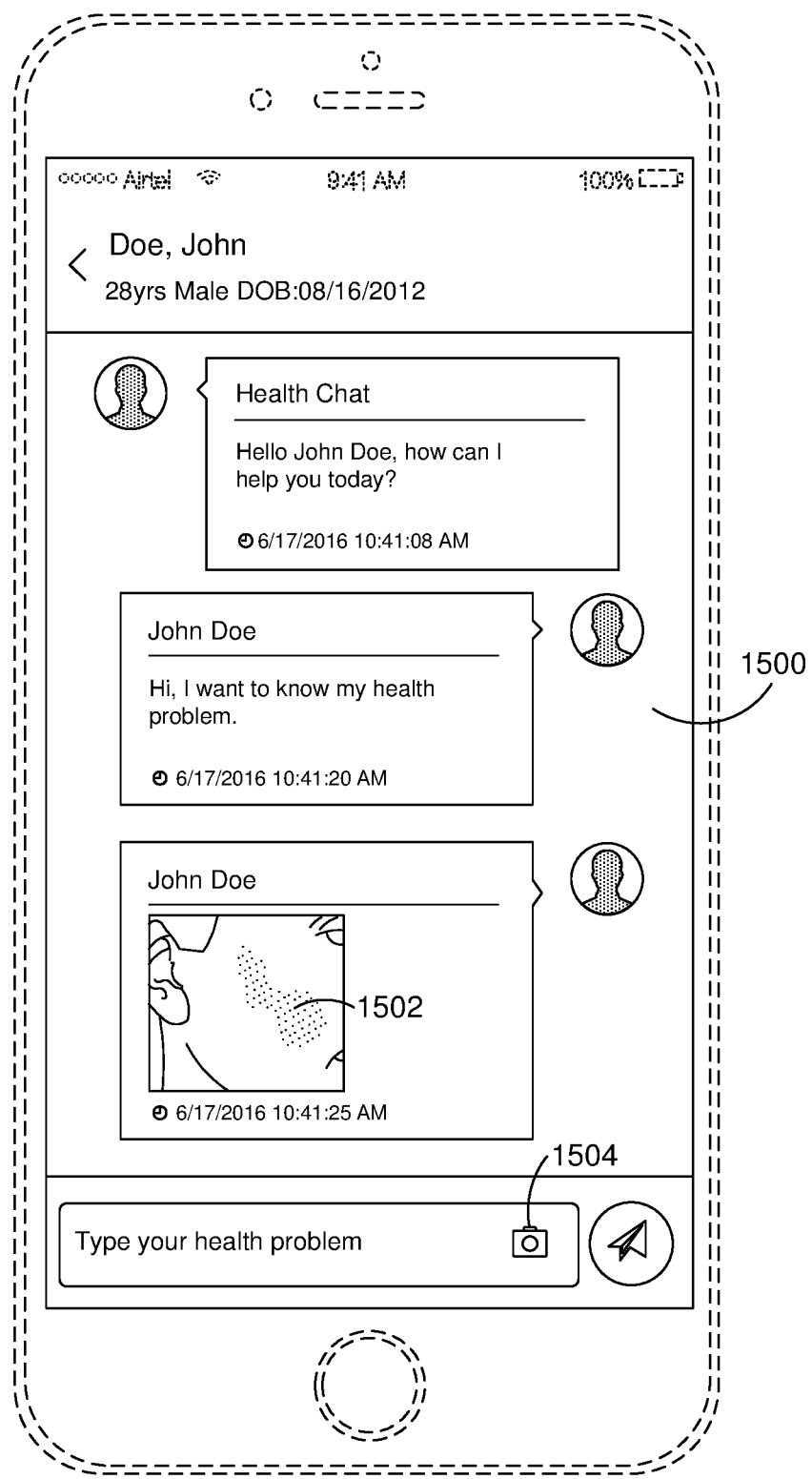
FIG. 15 is an exemplary illustration of a graphical user interface of a secure messaging service, in accordance with an embodiment of the present invention.

Additionally or alternatively, user input includes an image captured from the user device or stored on the user device, for example, as shown in the messaging GUI 1500 of FIG. 15. In such an embodiment, the user input image 1502 is processed to determine whether the image includes a recognizable part of the human body, such as a face, an eye, a hand, or the like. The user may select a camera GUI object 1504 to imitate camera functions at the user device and/or to input image data. The user input image is processed to identify symptoms that can be visually observed, such as skin conditions, abrasions, bruising, swelling of the eye or a joint, for example. The image may be segmented and analyzed relative to other images, for example, that are stored in a database or a repository as a sample image set. The analysis may include identification of objects in the image and recognition of other images have similar objects, facial recognition, and fingerprint identification, for example. The analysis may include using image tags to tag the user-provided image with symptoms and keywords. Keywords may be as identified based in user-input text and/or based on image tags associated with images that are determined to be similar to the user-provided image. The database or repository may be searched, using the user input image as a type of query, to identify one or more medical images that are similar to the user input image. In one embodiment, the secure messaging service analyzes the image in near real-time when the image is received.

In accordance with the method 200, all of the user input (e.g., including images, audio, and any negative inferences) and the medical events (e.g., the user's demographics and the user's family medical histories) are mapped to one or more medical conditions that are accurate and responsive to the user input, while also being specific to or customized for the user-specific electronic medical record and medical events therein, and which may be securely provided to the user device. To achieve this, the method 200 continues processing the user input using natural language processing. In some embodiments, the method 200 identifies contextual relationships between terms (e.g., non-keywords) in the user input based on the structure of the user input. The method 200 may also identify contextual relationships between terms in the user input and keywords identified during parsing, in some embodiments. The keywords and surrounding contextual clues may be compared to a database that stores semantic maps of medical terminology. Accordingly, in some embodiments, the method 200 may perform a semantic identification of medical terminology that corresponds to the one or more keywords. As such, the user input and the keywords are semantically analyzed in accordance with the method 200. In one embodiment, the method identifies medical terminology that semantically corresponds to the one or more keywords and recognizes whether the medical terminology is associated with the medical events in the electronic record. The method 200 may analyze the keywords and the user-specific electronic medical record against a plurality of differential diagnosis workflows, for example.

At block 214 of the method 200, keywords are mapped to medical events in the electronic medical record, including the user's demographics and the user's family medical histories, and to the any of the user selected portions from the image of the human body. Any user-input images are analyzed in the mapping process to identify keywords and/or medical events that accurately reflect or correlate to the visual content (e.g., skin condition) present of the images. Keywords that were used to tag or label audio data and/or image data (when present) may be mapped to medical events in the electronic medical record as well. Keywords and images are mapped to medical events that include and/or are related to the keyword or semantic equivalents, or that are relevant to the medical event based on computer learning, in embodiments. The mapping aspect is also performed in real or near-real time, as user input is received. The keywords and images may be mapped to medical events that are related to the selected portions of the image of the human body, in some embodiments. Mapping the one or more keywords to medical events and selected portions of the image of the human body further comprises performing a semantic analysis of the user input and the keywords, so that relevant medical terminology is identified, in some embodiments. In further embodiments, the method 200 includes recognizing one or more medical events in the electronic medical record that are related to the selected portion(s) of the image of the human body and recognizing medical terminology that corresponds to the one or more keywords. Further, a user-input image may be mapped to other images containing related or similar visual content and that are securely stored in the electronic medical record of the user, for example.

Continuing, the method 200 comprises identifying, from the mapping of the one or more keywords and any images (i.e., when provided), at least one medical condition associated with the one or more keywords, any images, and the one or more medical events, as depicted at block 216. The medical condition specifically reflects the medical events in the user-specific electronic medical record, including the user's demographics and the user's family histories. The at least one medical condition may be a current medical diagnosis that is already present in the electronic record of the user, the user's family medical histories, or it may correspond to a medical diagnosis present in a population health database. A population database may include plurality of electronic medical records corresponding to one or more segments of a population. The population database may be organized based on demographic information, as previously described. As such, when the user shares a particular demographic feature with at least one segment of the population (e.g., age group, gender, and/or diabetes type II), medical conditions stored in the population database or repository for the at least one segment may be mapped to the keywords and identified for the patient. In a further embodiment, database or repository is searched using the one or more keywords to identify medical conditions that are associated with the one or more keywords.

In embodiments of the method 200, the at least one medical condition is securely communicated to the user device to be displayed to the user, as shown at block 218. The medical condition is returned to the user device in near real-time within the context of the natural conversation facilitated by the secure messaging service. Because the medical condition(s) is/are informed by both the user input and the user-specific electronic medical record, the at least one medical condition exhibits increase accuracy in comparison to a user using one or more symptoms to conduct an internet search. Thus, inaccurate or inapplicable medical conditions are not included by way of this personalization.

Figure 16:
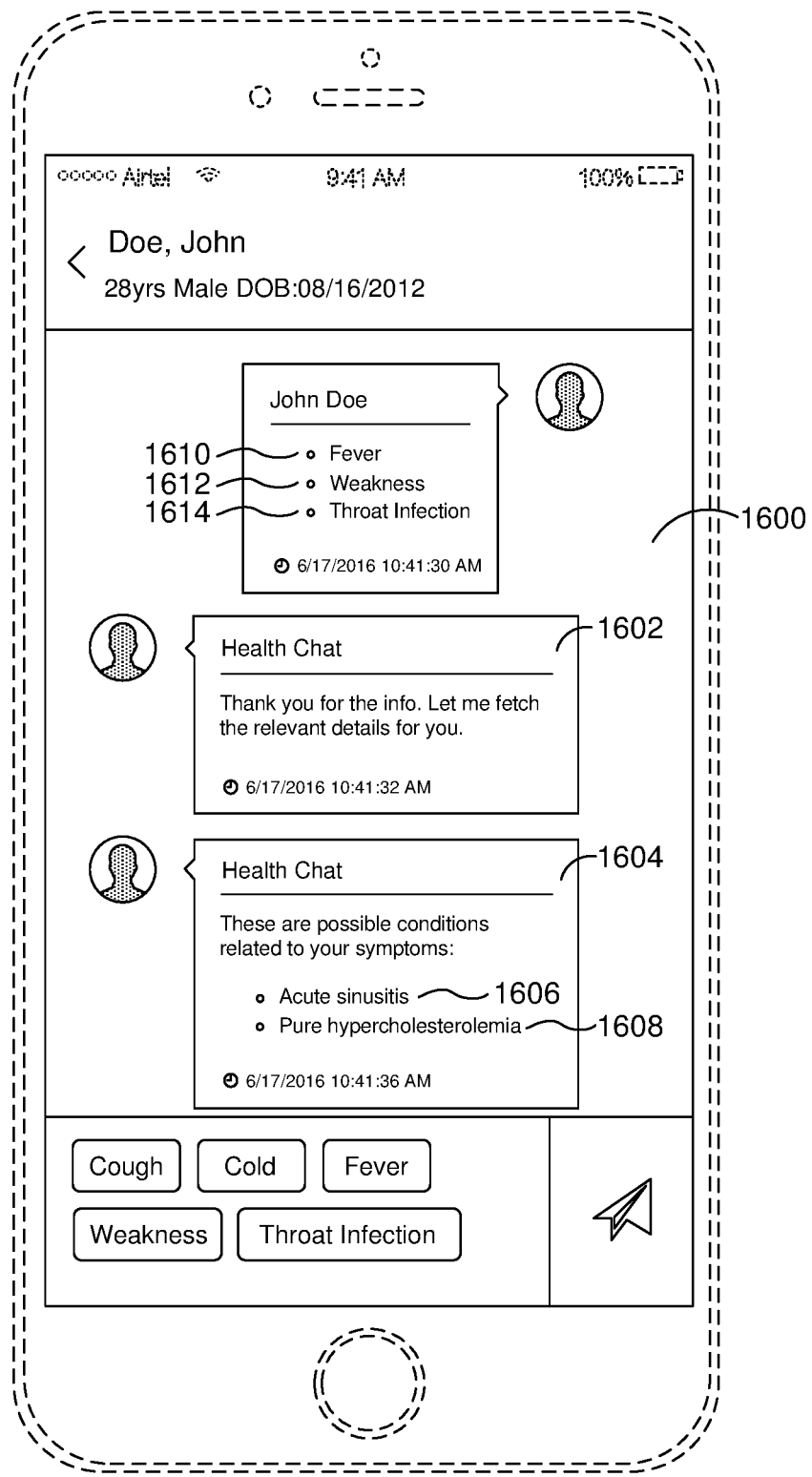
FIG. 16 is an exemplary illustration of a graphical user interface of a secure messaging service, in accordance with an embodiment of the present invention.

In one example, the predictive medical condition GUI 1600 of FIG. 16 presents a user with messages 1602, 1604 in order to confirm that the secure messaging service received the user input, that the user input is being or will be processed, and to present one or more medical conditions (e.g., Acute sinusitis 1606, Pure hypercholesterolemia 1608) to the user that the secure messaging service determined are responsive to the user input and are relevant based on the user-specific electronic medical record. The medical conditions are identified based on the parsing and mapping aspects of keywords 1610, 1612, 1614, for example, and a repository including differential diagnoses workflows. In further embodiments, the medical condition(s) is provided to the user device, to be displayed as a selectable link. Such a link may direct the user device to information about the at least one medical condition, for example. This information about the medical condition may be stored on a server and remotely retrieved by the user device.

Additionally or alternatively, the method 200 adds a new entry to the electronic medical record so that the new entry includes or documents the user input, the keyword(s), and/or the medical condition(s) so that the information may be retrieved at a future date (e.g., a medical visit). The user input is automatically stored in the electronic medical record of the user at the time the user input is submitted to the secure messaging service, in some embodiments. In embodiments, the entirety of the conversation is stored, including the full text (e.g., sentences) between the user and the secure messaging assistant. Accordingly, the user input is stored in the electronic medical record or other secure database by the secure messaging service so that text, keywords, and/or images provided by the user may be retrieved subsequently by a medical professional, for example, when the a visit is scheduled with a medical professional. In this way, a medical professional can review symptoms input or selected by the user, which provides the medical professional later review of the conversation and the user input as provided when initially seeking help through the secure messaging service. This review of the dialog by the medical professional allows the medical professional to make accurate diagnoses and treatment plans. The exemplary portion of computer programming code shown in FIG. 17 is illustrates code that supports the method 200, for example.

Figure 18:
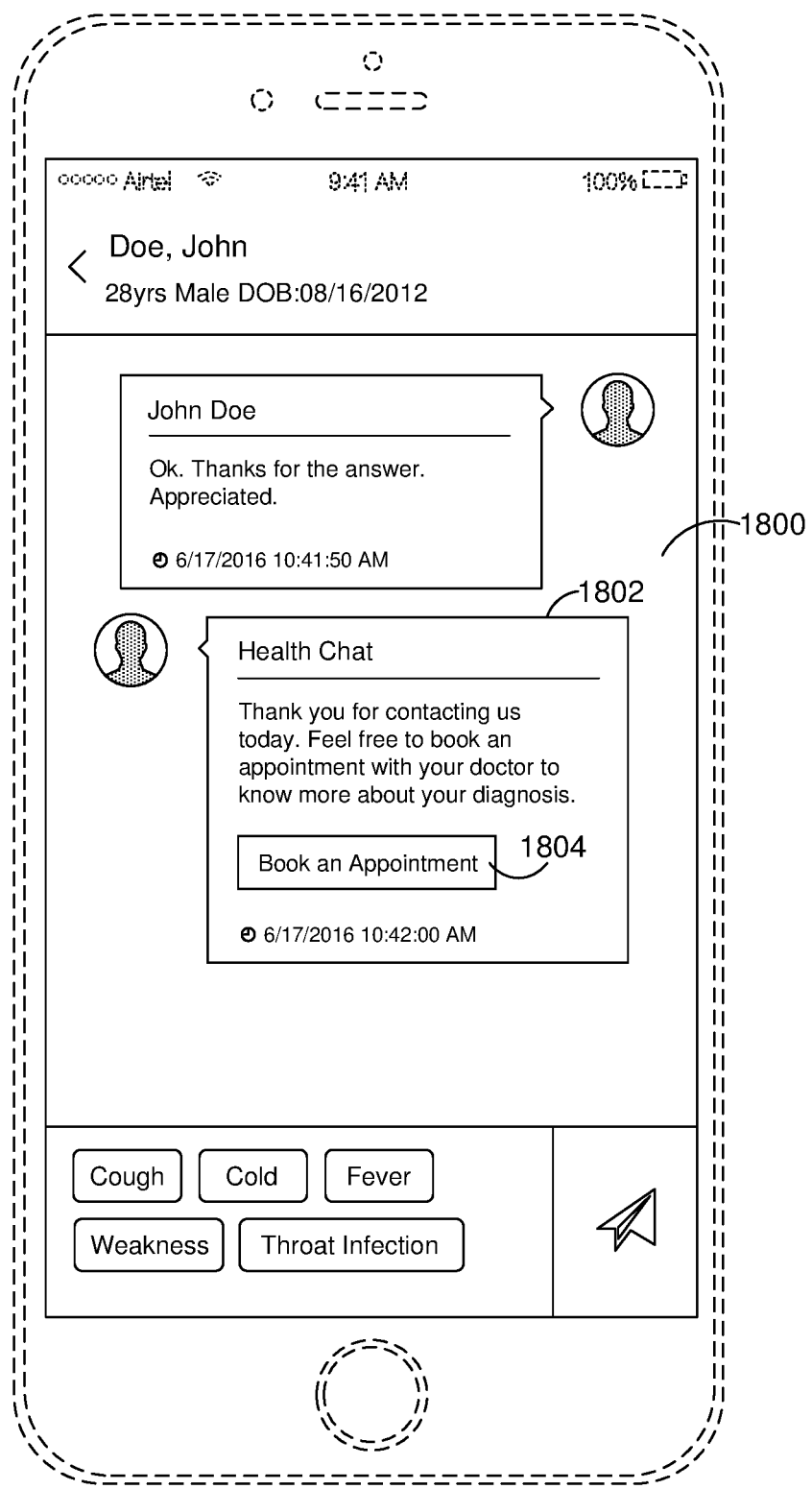
FIG. 18 is an exemplary illustration of a graphical user interface of a secure messaging service, in accordance with an embodiment of the present invention.

In some embodiments, the secure messaging assistant provides a user with an opportunity to schedule a medical visit through the application. The appointment GUI 1800 of FIG. 18 includes an exemplary message (e.g., Thank you for contacting us . . . 1802) that is displayed to a user and which includes a selectable GUI object (e.g., Book an Appointment GUI button 1804). In such embodiments, the secure messaging assistant generates a selectable GUI object that is a link to direct the user device to a scheduling assistant and provides the selectable GUI link to the user device. When an indication is received that the selectable link is selected, the secure scheduling assistant may access a schedule of a medical professional that is identified in the electronic medical record. The scheduling assistant may then provide, to the user device, a proposed time and date for an appointment and a name of the medical professional, for example.

Figure 19:
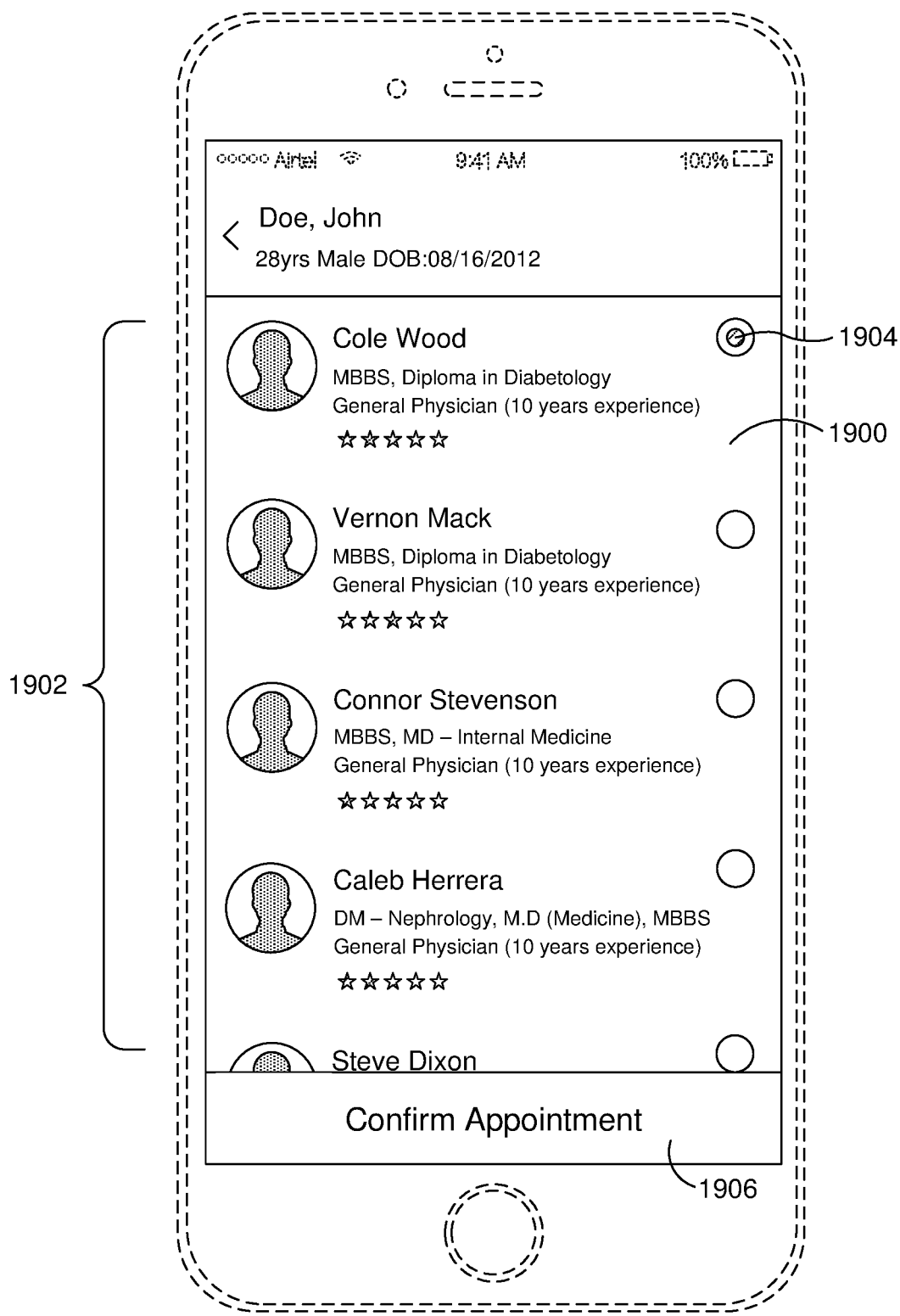
FIG. 19 is an exemplary illustration of a graphical user interface of a secure messaging service, in accordance with an embodiment of the present invention.
Figure 20:
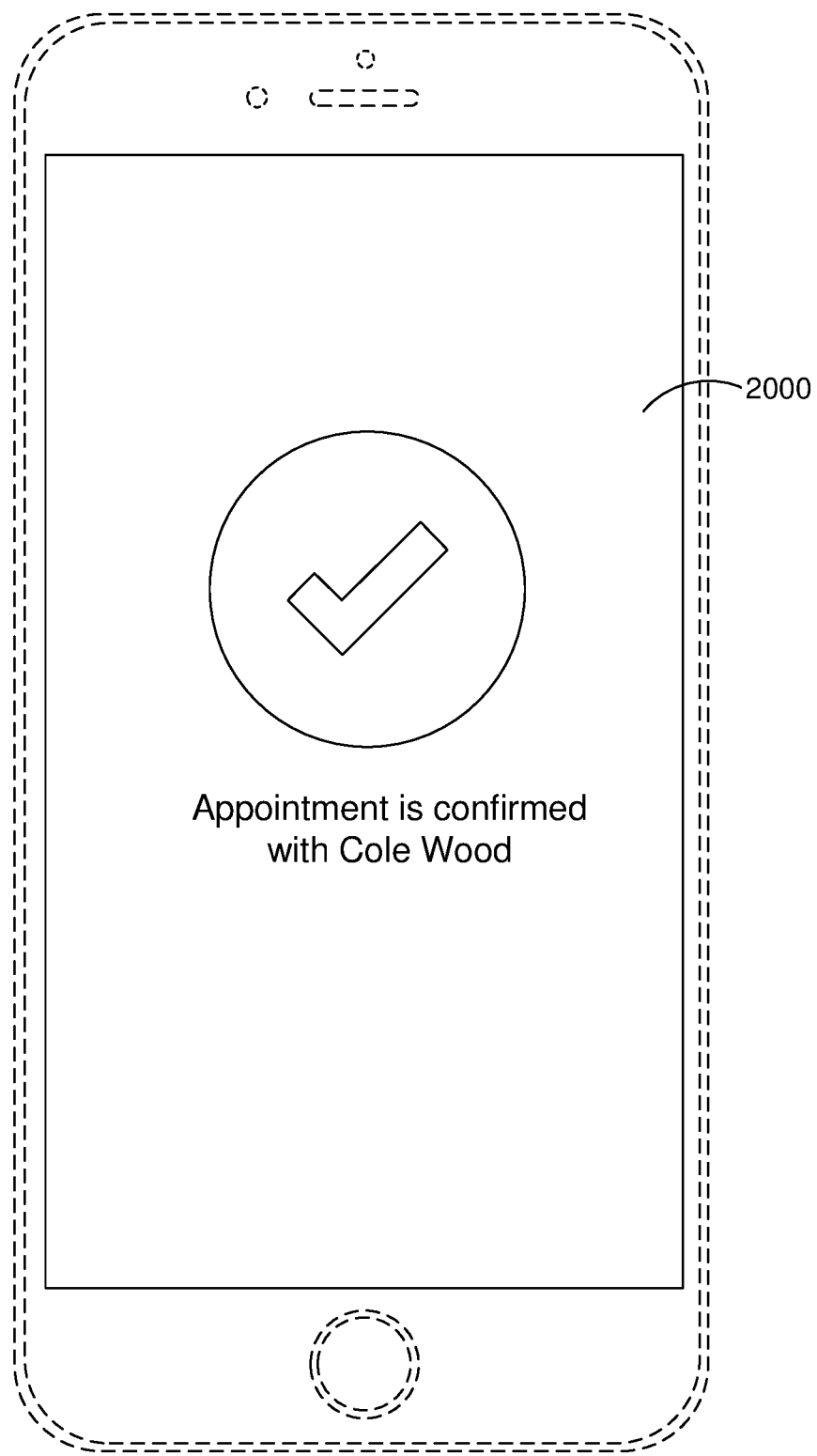
FIG. 20 is an exemplary illustration of a graphical user interface of a secure messaging service, in accordance with an embodiment of the present invention.

The exemplary selectable GUI object 1804 may, if selected, provide a user with a list of medical professionals 1902 as shown in the medical professional GUI 1900 of FIG. 19. In embodiments, the medical professional GUI 1900 presents medical professionals that are trained and able to treat one or more of the medical conditions identified via the mapping of user input and the user-specific electronic medical record, including the user's demographics and the user's family medical histories. For example, a list of pulmonologists is presented to the user when a respiratory disease is the identified medical condition, per the secure messaging service's analysis. The medical professional GUI 1900 may also include GUI objects, such as GUI object 1904, that a user may select, in order to indicate their desire to select a corresponding medical professional for the purpose of booking an appointment. A user may also select a GUI object (e.g., Confirm appointment GUI button 1906), for example, to confirm the appointment, in some embodiments. In embodiments, a portion or all of the conversation between the user and the secure messaging assistant are securely sent to a computing system (e.g., health record accessing system, calendar system) of the selected medical professional so that the medical professional may access and review the information before, during, and even after the scheduled appointment. Notably, the medical professional may review the symptoms input by a user, which the user may have forgotten by the time the scheduled appointment occurs. A confirmation GUI 2000, as shown in FIG. 20, may be presented to a user to provide positive visual feedback that the appointment has been or will be scheduled for the user. The user may then close or terminate the application on their device to end their interaction with the secure messaging service, in some embodiments.

The present invention has been described in relation to particular examples, which are intended in all respects to be illustrative rather than restrictive. From the foregoing, it will be seen that this invention is one well adapted to attain all the ends and objects set forth above, together with other advantages which are inherent to the system and method. It will be understood that certain features and subcombinations are of utility and may be employed without reference to other features and subcombinations. This is contemplated by and is within the scope of the claims.

What is claimed is:

1. A computer-implemented method comprising:
via one or more processors:
    causing an application that comprises a secure messaging automated assistant tool to load at a user device;
    receiving, via the application, user-identifying information for a user of the user device;
    identifying at least one medical event associated with the user at least by:
        retrieving a securely stored electronic medical record that is specific to an identity of the user in response to receiving the user-identifying information, the electronic medical record including user-specific medical information; and
        retrieving one or more medical events associated with the user from the electronic medical record;
    generating and causing display at the user device of the first graphical user interface of an image of a human body having a plurality of selectable portions;
    receiving, via the first graphical user interface, a selection of a selectable portion from the plurality of selectable portions to obtain a selected portion of the human body;
    mapping the one or more medical events to the selected portion of the human body to identify at least one medical event related to the selected portion of the human body;
    generating and causing display of a second graphical user interface in the application for the secure messaging automated assistant tool that generates a user customized prompt in response to receiving the selected portion of the human body and identifying the at least one medical event which prompts the user to provide text or voice user input at the user device for processing via natural language conversion;
    receiving, via the application, the text or voice user input via the secure messaging automated assistant tool on the second graphical user interface;
    parsing the text or voice user input using natural language processing to identify a plurality of symptom keywords;
    generating and causing display of a third graphical user interface in the application for the secure messaging automated assistant tool that presents the plurality of symptom keywords;
    receiving, via the application, user selection of one or more of the plurality of symptom keywords presented on the third graphical user interface, the user selection resulting in non-selection of one or more of the plurality of symptom keywords;
    generating and causing display of a fourth graphical user interface in the application for the secure messaging automated assistant tool that generates a plurality of more relevant and specific symptom keywords in response to the selection of the one or more symptom keywords, wherein the plurality of more relevant and specific keywords are generated using computer-learning analysis of the electronic medical record, the selected portion of the human body, the parsed text or voice user input, the selected one or more of the plurality of symptom keywords, and the non-selected one or more of the plurality of symptom keywords;
    receiving, via the application, user selection of one or more of the plurality of more relevant and specific symptom keywords presented on the fourth graphical user interface;
    identifying at least one medical condition corresponding to:
        (a) the selected portion of the human body;
        (b) the at least one medical event related to the selected portion of the human body;
        (c) the text or voice user input; and
        (d) the selected one or more of the plurality of symptom keywords and the selected one or more of the plurality of more relevant and specific symptom keywords, wherein the symptom keywords are different from the at least one medical condition and the more relevant and specific keywords are different from the at least one medical condition and the symptom keywords; and
    securely communicating the at least one medical condition to the user device and causing display to the user via the second graphical user interface.

2. The method of claim 1, further comprising:
identifying contextual relationships between terms in the text or voice user input based on structure of the text or voice user input.

3. The method of claim 1, further comprising:
identifying contextual relationships between terms in the text or voice user input and the one or more of the plurality of symptom keywords identified.

4. The method of claim 1, further comprising:
generating a selectable link that directs the user device to information about the at least one medical condition; and
providing the selectable link to the user device.

5. The method of claim 1, further comprising:
when the text or voice user input received via the secure messaging automated assistant tool includes an image captured from the user device, processing the image to recognize a corresponding portion of the human body; and
searching a repository for one or more medical images that are similar to the image captured from the user device.

6. The method of claim 1, further comprising:
adding a new entry to the electronic medical record, the new entry including one or more of the text or voice user input, the selected one or more of the plurality of symptom keywords, or the at least one medical condition, wherein the new entry is retrievable.

7. The method of claim 1, further comprising:
generating a selectable link to direct the user device to a scheduling assistant; and
providing the selectable link to the user device.

8. The method of claim 7, further comprising:
in response to receiving an indication that the selectable link was selected, accessing a schedule of a medical professional identified in the electronic medical record; and
providing, to the user device, a proposed time and date for an appointment and a name of the medical professional.

9. The method of claim 8, further comprising:
in response to receiving an indication to accept the proposed time and date for the appointment from the user device, adding a new entry to the schedule of the medical professional, the new entry including the at least one medical condition, wherein the new entry is retrievable.

10. The method of claim 1, wherein identifying at least one medical condition comprises:
executing a differential diagnosis workflow based at least one of: (a) the selected portion of the human body, (b) the at least one medical event related to the selected portion of the human body, or (c) the selected one or more of the plurality of symptom keywords.

11. The method of claim 1, wherein retrieving a securely stored electronic medical record includes retrieving the electronic medical record from a remote server.

12. The method of claim 1, wherein the at least one medical condition corresponds to a medical diagnosis from a population health database.

13. The method of claim 1, wherein the selected one or more plurality of symptom keywords correspond to symptoms being experienced by the user.

14. One or more non-transitory computer-readable storage media having computer-executable instructions embodied thereon that, when executed by one or more processors:
cause an application that comprises a secure messaging automated assistant tool to load at a user device;
receive, via the application, user-identifying information for a user of the user device;
identify at least one medical event associated with the user at least by:
retrieving a securely stored electronic medical record that is specific to an identity of the user in response to receiving the user-identifying information, the electronic medical record including user-specific medical information; and
retrieving one or more medical events, associated with the user, from the electronic medical record;
generate and cause display at the user device of a first graphical user interface of an image of a human body having a plurality of selectable portions;
receive via the first graphical user interface, a selection of a selectable portion from the plurality of selectable portions to obtain a selected portion of the human body; and
map the one or more medical events to the selected portion of the human body to identify at least one medical event related to the selected portion of the human body;
generate and cause display of a second graphical user interface in the application for the secure messaging automated assistant tool that generates a user customized prompt in response to receiving the selected portion of the human body and identifying the at least one medical event which prompts the user to provide user input at the user device for processing via natural language conversion;
receive, via the application, the text or voice user input via the secure messaging automated assistant tool on the second graphical user interface;
parse the text or voice user input using natural language processing to identify a plurality of symptom keywords;
generate and cause display of a third graphical user interface in the application for the secure messaging automated assistant tool that present the plurality of symptom keywords;
receive, via the application, user selection of one or more of the plurality of symptom keywords presented on the third graphical user interface, the user selection resulting in non-selection of one or more of the plurality of symptom keywords;
generate and cause display of a fourth graphical user interface in the application for the secure messaging automated assistant tool that generates a plurality of more relevant and specific symptom keywords in response to the selection of the one or more symptom keywords, wherein the plurality of more relevant and specific keywords are generated using computer-learning analysis of the electronic medical record, the selected portion of the human body, the parsed text or voice user input, the selected one or more of the plurality of symptom keywords, and the non-selected one or more of the plurality of symptom keywords;
receive, via the application, user selection of the one or more of the plurality of more relevant and specific symptom keywords presented on the fourth graphical user interface;
identify at least one medical condition corresponding to:
(a) the selected portion of the human body;
(b) the at least one medical event related to the selected portion of the human body;
(c) the text or voice user input; and
(d) the selected one or more of the plurality of symptom keywords and the selected one or more of the plurality of more relevant and specific symptom keywords, wherein the symptom keywords are different from the at least one medical condition and the more relevant and specific keywords are different from the at least one medical condition and the symptom keywords; and
securely communicate the at least one medical condition to the user device and cause display to the user via the second graphical user interface.

15. The computer-readable media of claim 14, further comprising:
   when the text or voice user input received via the secure messaging automated assistant tool includes audio data, perform a speech recognition analysis on the audio data;
   determine whether the audio data, as analyzed, includes at least one of the plurality of symptom keywords;
   when the audio data includes at least one of the plurality of symptom keyword, tag the audio data with the at least one of the plurality of symptom keywords; and
   store the audio data as a new entry in the electronic medical record that is specific to the user.

16. The computer-readable media of claim 14, further comprising:
   when the text or voice user input received via the secure messaging automated assistant tool includes an image, analyze the image; and
   tag the image with at least one of the plurality of symptom keywords.

17. The computer-readable media of claim 14, further comprising:
   recognize whether there are one or more of the medical events associated with the at least one of the plurality of portions of the human body selected from the image.

18. The computer-readable media of claim 14, further comprising:
   identify medical terminology that semantically corresponds to the plurality of symptom keywords; and
   recognize whether the medical terminology is associated with the medical events.

19. The computer-readable media of claim 14, further comprising:
   map the plurality of symptom keywords to the at least one medical condition.

20. The computer-readable media of claim 14, further comprising:
   extract the plurality of symptom keywords from the text or voice user input.

21. A system comprising:
   a database that securely stores electronic medical records including medical histories of a plurality of patients; and
   a server configured to:
      cause an application that comprises a secure messaging automated assistant tool to load at a user device;
      receive, via the application, user-identifying information for a user of the user device;
      retrieve a securely stored electronic medical record that is specific to an identity of the user in response to receiving the user-identifying information, the electronic medical record including user-specific medical information;
      retrieve one or more medical events, associated with the user, from the electronic medical record;
      provide an image of a human body having a plurality of selectable portions for display to the user at the user device of a first graphical user interface;
      receive via the first graphical user interface, a selection of a selectable portion from the plurality of selectable portions to obtain a selected portion of the human body;
      map the one or more medical events to the selected portion of the human body to identify at least one medical event related to the selected portion of the human body;
      generate and cause display of a second graphical user interface in the application for the secure messaging automated assistant tool that generates a user customized prompt in response to receiving the selected portion of the human body and identifying the at least one medical event which prompts the user to provide text or voice user input at the user device for processing via natural language conversion;
      receive, via the application, the text or voice user input via the secure messaging automated assistant tool on the second graphical user interface;
      parse the text or voice user input using natural language processing to identify a plurality of symptom keywords;
      generate and cause display of a third graphical user interface in the application for the secure messaging automated assistant tool that presents the plurality of symptom keywords;
      receive, via the application, the user selection of one or more of the plurality of symptom keywords presented on the third graphical user interface, the user selection resulting in non-selection of one or more of the plurality of symptom keywords;
      generate and cause display of a fourth graphical user interface in the application for the secure messaging automated assistant tool that generates a plurality of more relevant and specific symptom keywords in response to the selection of the one or more symptom keywords, wherein the plurality of more relevant and specific keywords are generated using computer-learning analysis of the electronic medical record, the selected portion of the human body, the parsed text or voice user input, the selected one or more of the plurality of symptom keywords, and the non-selected one or more of the plurality of symptom keywords;
      receive, via the application, user selection of one or more of the plurality of more relevant and specific symptom keywords presented on the fourth graphical user interface;
      identify at least one medical condition corresponding to:
         (a) the selected portion of the human body;
         (b) the at least one medical event related to the selected portion of the human body;
         (c) the text or voice user input; and
         (d) the selected one or more of the plurality of symptom keywords and the selected one or more of the plurality of more relevant and specific symptom keywords, wherein the symptom keywords are different from the at least one medical condition and the more relevant and specific keywords are different from the at least one medical condition and the symptom keywords; and
      securely communicate the at least one medical condition to the user device and cause display to the user via the second graphical user interface.

22. The system of claim 21, wherein the server is a Fast Healthcare Interoperability Resources (FHIR) server.

23. The system of claim 21, wherein the server is configured with an Healthcare Level 7 (HL7) compatible protocol to facilitate two-way secured communications between the secure messaging automated assistant tool and the user device.

* * * * *